(12) United States Patent
Lim et al.

(10) Patent No.: US 11,484,514 B2
(45) Date of Patent: Nov. 1, 2022

(54) MANUFACTURING METHOD OF AN HERBAL MEDICINAL TABLET FORMULATION FOR TREATING OBESITY WHICH CAN BE PRESCRIBED BASED ON SASANG CONSTITUTIONAL MEDICINE

(71) Applicants: NUBEBE CO., LTD., Seongnam-si (KR); HUMAN HERB CO., LTD., Daegu (KR)

(72) Inventors: Young Woo Lim, Seongnam-si (KR); Ji Myeong Ok, Seoul (KR); Woon Ho Lee, Daegu (KR); Young Bin Kim, Daegu (KR)

(73) Assignees: NUBEBE CO., LTD., Seongnam-si (KR); HUMAN HERB CO., LTD., Daegu (KR)

( * ) Notice: Subject to any disclaimer, the term of this patent is extended or adjusted under 35 U.S.C. 154(b) by 193 days.

(21) Appl. No.: 16/957,432

(22) PCT Filed: Dec. 20, 2018

(86) PCT No.: PCT/KR2018/016341
§ 371 (c)(1),
(2) Date: Jun. 24, 2020

(87) PCT Pub. No.: WO2019/132416
PCT Pub. Date: Jul. 4, 2019

(65) Prior Publication Data
US 2021/0069064 A1    Mar. 11, 2021

(30) Foreign Application Priority Data

Dec. 29, 2017 (KR) .................. 10-2017-0183328
Nov. 20, 2018 (KR) .................. 10-2018-0143446

(51) Int. Cl.
| | |
|---|---|
| *A61P 3/04* | (2006.01) |
| *A61K 36/346* | (2006.01) |
| *A61K 36/488* | (2006.01) |
| *A61K 36/882* | (2006.01) |
| *A61K 36/49* | (2006.01) |
| *A61K 36/8994* | (2006.01) |
| *A61K 36/31* | (2006.01) |
| *A61K 36/736* | (2006.01) |
| *A61K 36/8945* | (2006.01) |

(Continued)

(52) U.S. Cl.
CPC .............. *A61K 31/137* (2013.01); *A61J 3/06* (2013.01); *A61K 9/19* (2013.01); *A61K 9/28* (2013.01); *A61K 33/04* (2013.01); *A61K 36/076* (2013.01); *A61K 36/17* (2013.01); *A61K 36/185* (2013.01); *A61K 36/258* (2013.01); *A61K 36/284* (2013.01); *A61K 36/31* (2013.01); *A61K 36/346* (2013.01); *A61K 36/481* (2013.01); *A61K 36/488* (2013.01); *A61K 36/49* (2013.01); *A61K 36/534* (2013.01); *A61K 36/538* (2013.01); *A61K 36/54* (2013.01); *A61K 36/575* (2013.01); *A61K 36/62* (2013.01); *A61K 36/64* (2013.01); *A61K 36/65* (2013.01); *A61K 36/708* (2013.01); *A61K 36/725* (2013.01); *A61K 36/734* (2013.01); *A61K 36/736* (2013.01); *A61K 36/744* (2013.01); *A61K 36/752* (2013.01); *A61K 36/882* (2013.01); *A61K 36/884* (2013.01); *A61K 36/8945* (2013.01); *A61K 36/8994* (2013.01); *A61K 36/9068* (2013.01); *A61K 47/02* (2013.01); *A61K 47/46* (2013.01); *A61P 3/04* (2018.01)

(58) Field of Classification Search
None
See application file for complete search history.

(56) References Cited

U.S. PATENT DOCUMENTS

2008/0206368 A1 *   8/2008   Wang ................... A61K 36/87
                                                  424/766

FOREIGN PATENT DOCUMENTS

| CN | 1738633 | 2/2006 |
|---|---|---|
| CN | 105158194 | 12/2015 |

(Continued)

OTHER PUBLICATIONS

Al-Salihi (Ma Huang (Ephedrae Herba): Setting the Record Straight, Journal of Chinese Medicine • No. 110 • Feb. 2016, 18-30).*

(Continued)

*Primary Examiner* — H. Sarah Park
(74) *Attorney, Agent, or Firm* — Lex IP Meister, PLLC

(57) ABSTRACT

An embodiment of the present invention provides a manufacturing method of an herbal medicinal tablet formulation for treating obesity which is prescribed based on Sasang constitutional medicine, comprises manufacturing a concentrated ephedra powder agent so that an ephedrine content is 3.0-4.0%; determining a weight of the concentrated ephedra powder agent according to each constitution of Sasang constitutional medicine, and manufacturing a side effect-preventing powder agent for each constitution to prevent and suppress side effects according to constitution of Sasang constitutional medicine with respect to the weight of the concentrated ephedra powder agent; mixing the concentrated ephedra powder agent and the side effect-preventing powder agent with a variance of a weight ratio therebetween in consideration of weight, obesity, constitution of Sasang constitutional medicine, and side effects; and tableting the mixture of the prepared ephedra powder agent and side effect-preventing powder agent.

5 Claims, 11 Drawing Sheets

(51) Int. Cl.

| | |
|---|---|
| *A61K 36/185* | (2006.01) |
| *A61K 47/02* | (2006.01) |
| *A61K 47/46* | (2006.01) |
| *A61K 36/534* | (2006.01) |
| *A61K 36/744* | (2006.01) |
| *A61K 36/538* | (2006.01) |
| *A61K 36/708* | (2006.01) |
| *A61K 33/04* | (2006.01) |
| *A61K 36/64* | (2006.01) |
| *A61K 36/65* | (2006.01) |
| *A61K 31/137* | (2006.01) |
| *A61K 9/19* | (2006.01) |
| *A61K 36/258* | (2006.01) |
| *A61K 36/481* | (2006.01) |
| *A61K 36/284* | (2006.01) |
| *A61K 36/54* | (2006.01) |
| *A61K 36/9068* | (2006.01) |
| *A61K 36/076* | (2006.01) |
| *A61K 36/752* | (2006.01) |
| *A61K 36/725* | (2006.01) |
| *A61K 36/734* | (2006.01) |
| *A61K 36/575* | (2006.01) |
| *A61K 36/884* | (2006.01) |
| *A61J 3/06* | (2006.01) |
| *A61K 9/28* | (2006.01) |
| *A61K 36/17* | (2006.01) |
| *A61K 36/62* | (2006.01) |

(56) References Cited

FOREIGN PATENT DOCUMENTS

| | | |
|---|---|---|
| JP | 2012-531446 | 12/2012 |
| KR | 10-2004-0107544 | 12/2004 |
| KR | 10-2007-0034561 | 3/2007 |
| KR | 10-2008-0004420 | 1/2008 |
| KR | 10-2009-0011597 | 2/2009 |
| KR | 10-2009-0132948 | 12/2009 |
| KR | 10-2010-0067299 | 6/2010 |
| KR | 10-2012-0094989 | 8/2012 |
| KR | 10-1212635 | 12/2012 |
| KR | 10-1290222 | 7/2013 |
| KR | 10-2013-0126380 | 11/2013 |
| KR | 10-2014-0112772 | 9/2014 |
| KR | 10-1442711 | 9/2014 |
| KR | 10-1573510 | 12/2015 |
| KR | 10-1672251 | 11/2016 |

OTHER PUBLICATIONS

Bong-Soo Kim, "The anti-obesity effect of Ephedra sinica through modulation of gut microbiota in obese Korean women", Journal of Ethnopharmacology, vol. 152, 2014, pp. 532-539.
Shan, Xibin, Pharmaceutical Engineering, pp. 373-374, Aug. 31, 1998.
SIPO, Office Action of CN 201880084405.4 dated Sep. 28, 2021.
SIPO, Office Action of CN 201880084312.1 dated Nov. 10, 2021.
Jin, Mingyu, Korea Medicine in China—Volume of Prescriptions, pp. 60-61, Dec. 31, 2015.
Xu, Yujin, Korea Medicine in China—Volume of Fundamental Theories, pp. 86-88, Dec. 31, 2015 (English translation only).
Anonymous, Naver Blog, Dec. 22, 2017, URL: https://blog.naver.com/chanelyk/221168838052.
Ga-Won Jo, et al., "Review on the Efficiency and Safety of Mahuang and Ephedrine in the Treatment of Obesity-Focused on RCT-", Journal of Korean Medicine, vol. 38, No. 3, pp. 170-184, Sep. 5, 2017.
The Korean Pharmacopoeia(Tenth Edition), Ministry of Food and Drug Safety, [Notification Sep. 2012, Mar. 26, 2012].
Mi-Ja Hwang, et al., "Literature Review of Herbal Medicines on Treatment of Obesity Since 2000—Mainly about Ephedra Herba", Journal of Society of Korean Medicine for Obesity Research 2007:7(1):39-54.
D Molnar, et al., "Safety and efficacy of treatment with an ephedrine/caffeine mixture. The first double-blind placebo-controlled pilot study in adolescents", International Journal of Obesity 24, 1573-1578, Dec. 4, 2000.
Ann G Liu, et al., "The Effect of Leptin, Caffeine/Ephedrine and their Combination Upon Visceral Fat Mass and Weight Loss", Obesity, vol. 21, Iss. 10, pp. 1991-1996, May 19, 2013.
Tae-ho Lee, et al., "Adverse Effects of Ephedra According to Sasang Typology in Healthy Adults: A Double-Blind Randomized Controlled Trial", Korean J. Orient. Int. Med. 30(1):144-152 (2009).
Seo-Young Kim, "Oriental medical treatment for Obesity: A systematic review and meta-analysis" Thesis for the Degree of Master of Korean Medicine, Department of Clinical Korean Medicine, Graduate School, Kyung Hee University, Seoul, Korea, Feb. 2018.
F. L. Greenway MD, "The safety and efficiency of pharmaceutical and herbal caffeine and ephedrine use as a weight loss agent", Obesity reviews 2, 199-211, Jan. 15, 2001.
Jinju Yeo, "Effects of Mahuang for Weight Loss in Healthy Adults: A Double-Blind, Controlled, Randomized, Chinical Trial", Department of Korean Medicine, Graduate School of Woosuk University.
Yun-Kyung Song, et al., "Clinical Application of Ma Huang in the Obesity Treatment", Journal of Society of Korean Medicine for Obesity Research 2007:7(1):1-7.
Mi-Young Song, et al., "The Safety Guidelines for use of Ma-huang in Obesity Treatment", Journal of Korean Oriental Association for Study of Obesity 2006:6(2):17-27.
Hojun Kim, et al., "A Clinical Practice Guideline for Ma-huang (Ephedra sinica) Prescription in Obesity", Journal of Society of Korean Medicine for Obesity Research 2007:7(2):27-37.

* cited by examiner

MANUFACTURING METHOD OF AN HERBAL MEDICINAL TABLET FORMULATION FOR TREATING OBESITY WHICH CAN BE PRESCRIBED BASED ON SASANG CONSTITUTIONAL MEDICINE

TECHNICAL FIELD

Background Art

(a) Field of the Invention

The present invention relates to a manufacturing method of an herbal medicinal tablet formulation for treating obesity which can be prescribed based on Sasang constitutional medicine, and more particularly, to a manufacturing method of an herbal medicinal tablet formulation for treating obesity and being able to be prescribed based on Sasang Medicine (hereinafter also referred to as "Gambijeong") that may confirm clinical effectiveness of weight loss while using the same amount of medicine as a desired prescription, may maintain safety of the herbal medicine by quantifying an index component for the first time among components of diet herbal medicines and controlling an abnormal reaction to the medicine, may maintain a stable treatment rate for each individual treatment and body weight/obesity by preparing a medicine by a quantitative and standardized method considering constitution and weight/obesity based on Sasang constitutional medicine, and may solve problems of a typical oriental medicine diet, such as a peculiar smell or bitter taste of oriental medicine, and inconvenience of taking such as an excessive dose.

(b) Description of the Related Art

*Ephedra sinica* Stapf (ephedra) is a perennial shrub of the ephedra family of which the grass stem is dried and is medicinal, and is a medicine that has been mainly used in Korean medicine for fever, chronic cough, asthma, and edema.

A main component of ephedra is composed of alkaloids such as L-ephedrine, pseudoephedrine, norephedrine, and norpseudoephedrine, and of these, ephedrine is the largest component at 30 to 90% of total alkaloids.

Ephedrine has a sympathetic nervous system excitatory effect that suppresses appetite, increases heat and metabolism, inhibits cholesterol absorption in the small intestine, and accelerates body fat breakdown by increasing energy consumption in adipose tissue.

Due to ephedrine's sympathetic nervous system excitatory effect, *Ephedra sinica* Stapf is associated with causing cardiovascular, autonomic nervous system, and digestive system symptoms such as headache, tachycardia, elevated blood pressure, and nausea, and thus, it is forbidden to be used as a food in Korea, like in the United States, and is used only as a medicine under a professional prescription of an oriental medicine doctor.

Due to safety concerns due to a side effects of the *Ephedra sinica* Stapf, use of the *Ephedra sinica* Stapf in Korea and its capacity issues have been raised both inside and outside the oriental medicine field, thus, in 2007, the society of Korean medicine for obesity research has developed clinical practice guidelines for use of *Ephedra sinica* Stapf for treatment of obesity and weight loss.

However, only a maximum allowable daily dose of ephedrine has been described, and there is a lack of usefulness in actual clinical practice because specific and clear criteria are not presented.

A total alkaloid content in ephedra is 0.5 to 2.5%, and the Korean Pharmacopoeia stipulates that the total alkaloid (ephedrine and caustic ephedrine) content in ephedra should be at least 0.7%.

However, a content of ephedrine in total alkaloids of ephedra varies from 30 to 90% depending on the harvesting time and growth environment, and when comparing an ephedrine extraction amount at a time of ephedra decoction, since the amount of ephedrine in a control decoction solution containing ephedra corresponds to 73 to 96% of the ephedra's sole decoction solution, an actual ephedrine content varies considerably depending on a country of origin of a medicinal material, a formulation, a decocting process, or a condition of absorption distribution, and for this reason, since a blood concentration of a patient may vary, both stability of a medicine and safety of treatment act as a considerably unstable factors.

Generally, in the oriental constitutional medicine, the constitution is classified according to strength and weakness of organs, and especially in a case of Taeeumin, Soeumin, and Soyangin, constitutional physiological characteristics significantly affect obesity. Since Taeeumin have a large liver and small lungs, they have strong nutrient absorption and is easy for them to gain weight, while their ability to dissipate and discharge heat and waste products is poor; since Soeumin have large kidneys and a small spleen, their digestive absorption is weak, and their muscle mass is insufficient, resulting in poor metabolism; and since Soyangin have a large spleen and small kidneys, they have severe stress binge eating and poor detoxification and excretion functions, so they need a prescription for obesity while considering their constitution. Pathophysiological characteristics of obesity according to specific constitution are as follows.

According to the characteristics of obesity of Taeeumin, compared to other constitutions, Taeeumin have vigorous digestive function and intestinal absorption, and their average BMI is highest among the constitutions, and their moderate or high obesity rates are highest. Taeeumin experience large body weight changes, severe swelling, and have a lot of visceral fat, as well as fat in the sides, buttocks, and thighs; their waist-hip ratio (WHR) is high, and metabolic circulation is lowered, so adult diseases such as hypertension, paralysis, hyperlipidemia, and fatty liver are often accompanied; and Taeeumin have a good and large liver, have void and small lungs, and have a wet constitution, and the skin, lungs, and respiratory organs are weak, so atrophy, allergic dermatitis, rhinitis, bronchial asthma, and hives are likely to occur.

In addition, according to the obesity characteristics of Soeumin, they have weak gastrointestinal function compared to other constitutions, and digestive disorders are easily generated due to poor intestinal motility; they often have constipation or diarrhea, and their average BMI among the constitutions is the lowest; and Korean-style obesity (thin obesity) often occurs due to lack of exercise and lack of muscle mass due to poor metabolism. Therefore, there is a large decrease in basal metabolism due to the lack of muscle mass, and there are a large number of weakness-type constitutions that suffer from chronic fatigue due to weak physical strength and sensitivity. The decrease in metabolic function due to low muscle mass generally occurs in the constitution that suffers from the most side effects (low blood sugar symptoms such as dizziness and fatigue) when dieting, and Soeumin constitutionally lack energy so blood circulation falls and the hands and feet are cold, and further, they are sensitive to cold. In this body type, the upper body is poor and looks dwarfed overall, the abdomen and thigh lower body obesity are relatively high, and they suffer a lot from lower body edema.

According to the characteristics of obesity of Soyangin, they have a good and large spleen, and void and small kidneys, and they have a representative fever constitution and good digestive powers, but have poor control over stress, which may lead to stressful binge eating, gastritis caused by binge drinking, and digestive problems. In case of frequent drinking or frequent night eating, it is easy to be exposed to diseases such as reflux esophagitis and gastric ulcers. Digestion is good, but excretion is poor, so probability of constipation is higher than for other constitutions. Body fat is mainly concentrated in the upper body, and the lower body is poor, which may cause degenerative diseases of the lumbar spine and degenerative knee arthritis due to obesity. The upper body is strong, the lower body is slim, and there are many body types with the abdomen expanded in the forward direction.

On the other hand, it is a great advantage and feature that the herbal medicine formulation is prepared with various mixing ratios according to respective medicines and a degree of disease and a constitution of a patient, even for the same disease, however most herbal medicine formulations are used as a propellant, a pill, a powder, a granule formulation, a concentrated liquid formulation, and a distillate, so the yield of an extract is not constant and it is difficult to confirm clinical effectiveness; in addition, it is uncomfortable to eat with a peculiar herbal odor or bitter taste after taking it and an excessive amount thereof, and further, it is inconvenient to store, so diet herbal medicine formulations are not easily used.

DISCLOSURE

Technical Problem

The present invention has been made in an effort to provide an herbal medicinal tablet formulation for treating obesity which can be prescribed based on Sasang constitutional medicine, and more particularly, to an herbal medicinal tablet formulation for treating obesity being able to prescribed based on Sasang Medicine (hereinafter also referred to as "Gambijeong") that may confirm clinical effectiveness of weight loss while using the same amount of medicine as a desired prescription, may maintain safety of the herbal medicine by quantifying an index component for the first time among components of diet herbal medicines and controlling an abnormal reaction of the medicine, may maintain a stable treatment rate for each individual treatment and body weight/obesity by preparing a medicine by a quantitative and standardized method considering constitution and weight/obesity based on Sasang constitutional medicine, and may solve problems of a typical oriental medicine diet, such as a peculiar smell or bitter taste of oriental medicine, and inconvenience of taking it such as an excessive dose.

Technical Solution

An embodiment of the present invention provides a manufacturing method of an herbal medicinal tablet formulation for treating obesity which can be prescribed based on Sasang constitutional medicine, comprises manufacturing a concentrated and quantified ephedra powder agent so that an ephedrine content of ephedra, which differs from 0.5-2.5% depending on a producing district and collecting period, is 3.0-4.0%, determining a weight according to each constitution of Sasang constitutional medicine of the concentrated and quantified ephedra powder agent of which the ephedrine content is 3.0-4.0%, and manufacturing a side-effect-preventing powder agent for each constitution to prevent and suppress side effects according to constitution of Sasang constitutional medicine with respect to the weight of the ephedra powder agent, preparing the ephedra powder agent and the side-effect-preventing powder agent while varying a weight ratio therebetween in consideration of weight, obesity, constitution of Sasang constitutional medicine, and side effects while mixing the ephedra powder agent and the side-effect-preventing powder agent; tableting a mixture of the prepared ephedra powder agent and side-effect-preventing powder agent; coating the tableted ones after tableting; and after the coating, while sorting out defective ones from coated ones and packaging, displaying a label including information prepared according to weight, obesity, constitution of Sasang constitutional medicine, and side effects.

When the ephedrine content is constant at 3-4%, a weight of the ephedra powder agent is about 360 g for Taeeumin, about 297 g for Soeumin, and about 360 g for Soyangin, and a weight ratio of the side-effect-preventing powder agent for each constitution with respect to a weight of the ephedra powder agent is about 1:8-10 for Taeeumin, about 1:9-11 for Soeumin, and about 1:8-10 for Soyangin, and the ephedrine content is, based on one day, 60 to 90 mg for normal weight, overweight, and initial obesity; 80 to 120 mg for overweight and obesity, 90 to 120 mg for moderate and extreme obesity, and 130 to 140 mg for tolerance, moderate, and extreme obesity.

The manufacturing of the concentrated and quantified ephedra powder agent so that the ephedrine content is 3.0-4.0% includes primarily quantifying the ephedrine content to be 7 to 8 Brix through Brix measurement every 2 hours in a hydraulic decocting process; and secondarily quantifying the ephedrine content to be 30 to 35 Brix through Brix measurement every 2 hours in a low temperature vacuum concentration process.

The filtering a foreign matter through a sieve with a 45 mesh scale may be further included after the secondarily quantifying, the manufacturing of the concentrated and quantified ephedra powder agent so that the ephedrine content is 3.0-4.0% further includes lyophilizing the ephedra powder agent of 30 to 35 Brix that is secondarily quantified, and in the lyophilizing, a freezing condition is 8 hours at a temperature of −30 to −40° C., and a drying condition is at least 60 hours at a temperature of 30 to 40° C., and measuring and labeling an ephedrine content of the lyophilized ephedra powder agent, and airtightly packing the lyophilized ephedra powder agent and side-effect-preventing powder agent for each constitution.

Advantageous Effects

According to the embodiment of the present invention, it is possible to provide an herbal medicinal tablet formulation for treating obesity being able to prescribed based on Sasang Medicine that may confirm clinical effectiveness of weight loss; that may maintain safety of the herbal medicine by quantifying the index component among the components of a diet herbal medicine and controlling an abnormal reaction of the medicine regardless of the collection time, growth environment, mixture, or conditions of a decocting process or absorption distribution; that may shorten a treatment period within less than 3 months compared to other western medicine or oriental medicines; that may maintain personalized treatment and a stable treatment rate for each weight/obesity by quantified and standardized usage considering constitution, weight, and obesity according to Sasang constitutional medicine; and that may solve the problems of the traditional oriental medicine diet, such as the peculiar smell, bitterness, excessive doses, and discomfort of taking of the traditional oriental medicine.

MODE FOR INVENTION

Figure 1:
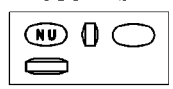
FIG. 1 illustrates a photograph of an herbal medicinal tablet formulation for treating obesity which can be prescribed based on Sasang constitutional medicine according to an embodiment of the present invention.
Figure 1:
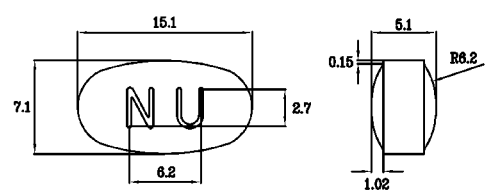
Figure 1:
Figure 1:
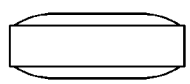
Figure 1:

Hereinafter, the present invention will be described more fully with reference to the accompanying drawings, in which exemplary embodiments of the invention are shown. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

In the present specification, unless explicitly described to the contrary, the word "comprise" and variations such as "comprises" or "comprising" will be understood to imply the inclusion of stated elements but not the exclusion of any other elements.

First, as shown in FIG. 1, an herbal medicinal tablet formulation for treating obesity which can be prescribed based on Sasang constitutional medicine according to an embodiment of the present invention has the same hardness as a typical tablet formulation; is quickly disintegrated without burdening the stomach when taken with water; has a size of 5.00±30 mm, which is about half the size of a typical tablet formulation, while it has a rectangular shape so that the neck does not feel pain when taking it due to characteristics of an herbal medicine with a large or rough surface; and has a disintegration time within 30 minutes and hardness of about 12.0 kp.

The following Experimental Example 1 was performed on 100 patients who visited the oriental medical clinic of the present applicant in order to configure the herbal medicinal tablet formulation for treating obesity which can be prescribed based on Sasang constitutional medicine according to the embodiment of the present invention described above.

Experimental Example 1

In order to configure the herbal medicinal tablet formulation for treating obesity which can be prescribed based on Sasang constitutional medicine according to the embodiment of the present invention described above, commercially available round, rectangular, triangular, and square tablet formulation shapes; tablet formulations of a typical size, ½ size, and less than ½ size; disintegration times of 20 minutes, 30 minutes, 40 minutes, and a hour; a degree of smearing on the hand; and preference of hardness were determined as very good, good, normal, and bad, and are shown in Table 1.

Table 1 shows the results of investigation for the size, the disintegration degree, the degree of smearing on the hand, and the preference of hardness of the herbal medicinal tablet formulation for treating obesity which can be prescribed based on Sasang constitutional medicine according to the embodiment of the present invention

TABLE 1

| | Very good | Good | Normal | Bad |
| --- | --- | --- | --- | --- |
| Shape | Rectangle 7 | Rectangle 17 | Rectangle 34 | 42 people prefer different shapes |
| Size | ½ general size 20 | ½ general size 31 | ½ general size 19 | 30 people prefer about general size or about half or less the general size |

TABLE 1-continued

|  | Very good | Good | Normal | Bad |
|---|---|---|---|---|
| Disintegration | Within 30 minutes 18 | Within 30 minutes 23 | Within 30 minutes 29 | Prefer within 20 minutes |
| Degree of smearing on hand and hardness | Degree of not being smeared on hands and not easily broken 17 | Degree of not being smeared on hands and not easily broken 24 | Degree of not being smeared on hands and not easily broken 27 | |

As shown in Table 1, it was found that 58 out of 100 ordinary people had a preference of 'Normal' or more for the rectangular shape; that as for the size, 70 people had a preference of 'Normal' or more for about ½ or less than the typical size; that as for the load hardness and the degree of disintegration, 68 people preferred the same hardness as that of the typical tablet formulation and the degree of disintegration that was not smeared on hand and was easily broken; and that 70 people preferred it to disintegrate in water within 30 minutes.

As a result, the herbal medicinal tablet formulation for treating obesity which can be prescribed based on Sasang constitutional medicine according to the embodiment of the present invention was a rectangular tablet formulation and could be prescribed to be stored in a plastic containers for one month; it could be taken with water after meals; it was an herbal medicine, but there was no concern about deterioration when exposed to air, and it was not bulky; and it could solve the problems that may occur when taking common herbal medicines by rapid disintegration, without problems such as smearing when picking up by hand or the peculiar smell or difficult swallowing of typical herbal medicines.

On the other hand, the herbal medicinal tablet formulation for treating obesity which can be prescribed based on Sasang constitutional medicine according to the embodiment of the present invention increased the ephedrine content, which was the target substance (active ingredient) that provided the effect of reducing obesity, to 3.0-4.0% compared to 0.5 to 2.5% that was the content of natural ephedra; it included the ephedra powder agent that achieves medicinal effect stability by maintaining the constant ephedrine content, the side-effect-preventing powder agent for each constitution prescribed by taking into consideration the characteristics of Sasang constitutional medicine constitution, that is, Soeumin, Taeeumin, Soyangin, and Taeyangin in order to alleviate the side effect of the ephedra powder agent, and the disintegrant to provide the hardness and disintegration time corresponding to that of the typical tablet formulation; and the weight ratio of the ephedra powder agent and the side-effect-preventing powder agent for each constitution (hereinafter also referred to as "Gambisan") was 8-10:1 to 9-11:1.

According to a paper published in September of 2017 in the Journal of Korean Medicine [A Study on the Effectiveness and Stability of Ephedra and Ephedrine in the Treatment of Obesity-Focused on RCT Research], the ephedra and ephedrine-administered groups showed weight and body fat loss when compared to the control group when taken for 20 weeks or more. According to a paper published in 2000 in the International Journal of Obesity, "Safety and efficacy of treatment with an ephedrine/caffeine mixture. The first double-blind placebo-controlled pilot study in adolescents.", compared to the control group, it was found that the combination of ephedrine and caffeine showed a significant weight loss effect; and according to a paper published in 2013 in the international journal "Obesity", "The Effect of Leptin, Caffeine/Ephedrine and their Combination Upon Visceral Fat Mass and Weight Loss.", during the 25-week study period, the combination formulation containing ephedrine showed a significant weight loss effect compared to the leptin alone formulation, and in most cases, there was the inconvenience of maintaining the prescription for about 6 months.

The herbal medicinal tablet formulation for treating obesity which can be prescribed based on Sasang constitutional medicine according to the embodiment of the present invention may be approved by the U.S. FDA up to pseudoephedrine at 240 mg/day, and ephedrine at 150 mg/day for OTC medicine; in the treatment of obese patients, when 5% of the initial weight is lost within 3 months, the effectiveness of the medicine is recognized, and when 10% thereof is lost, successful weight loss is recognized; and particularly, since 5-10% of weight loss may improve obesity-related diseases and reduce complications, the clinical practice guidelines from the Korean Society for Obesity make it possible to achieve an effective obesity reduction effect within 3 months within the range of 150 mg/day, the US FDA-allowed ephedrine content, considering that the goal of weight loss in obese patients is to target 5-10% of their initial weight loss over the course of 3-6 months.

In addition, with respect to the herbal medicinal tablet formulation for treating obesity which can be prescribed based on Sasang constitutional medicine according to the embodiment of the present invention, the lipase activity experiment of Experimental Example 4 below was performed, and it was confirmed that the lipase activity was inhibited as the ephedrine content increased; and through Experimental Example 2, while effective ephedrine content within the range of 150 mg/day, which is the US FDA-allowed ephedrine content, achieved effective weight loss within 3 months for each constitution classified as Soeumin, Soyangin, Taeeumin, and Taeyangin, it was possible to determine the weight ratio of the appropriate ephedra powder and side-effect-preventing powder agent for each constitution with few side effects.

First, the prescription of side-effect-preventing powder agent for each constitution to eliminate each constitutional side effect of ephedra according to Sasang constitutional medicine is as follows.

As shown in Table 2 below, the prescription for the side-effect-preventing powder agent for each constitution was based on the ephedra weight of 1, and had the pharmacological effect supplemented by considering the side effects that occur during diet by constitution, wherein the prescription included medicinal content confirmed through long-term clinical experience, the Sasang Constitutional Journal, the Korean Oriental Internal Medicine Journal, the Botanical List, the Korean Oriental Medicine Journal, and theses.

Table 2 shows the constitutional side effect of Sasang constitutional medicine, the prescription of the side-effect-preventing powder agent for each constitution for preventing this side effect, and the pharmacological effect of each medicinal content.

TABLE 2

| Constitutional side effect | Constitutional side-effect-preventing powder agent | Pharmacological effect of each herb |
|---|---|---|
| Taeeumin Occurrence of atopic dermatitis, allergic dermatitis, rhinitis, bronchial asthma, urticaria, etc. due to weak skin, lungs, and respiratory system | Taeeumin prescription for side-effect-preventing powder agent for each constitution: alisma 1, platycodon 1, puerariae 1, acorus gramineus1, castanea mollissima 2, coicis semen 2, semen raphani 1, semen armeniacae amarum 1, cinnamon-vine 2, semen nelumbinis 2 | Gastrointestinal endocrine cell function regulation Anti-lipid effect, antioxidant effect, anti-inflammatory effect on allergic reaction Anti-obesity effect |
| Soyangin Clinically, constipation, acne, urinary inflammation, etc. occurrence | Soyangin prescription for side-effect-preventing powder agent for each constitution: talcum 2, plaster 1, peppermint 1, gardeniae fructus 1, schizonepeta 1, rhubarb 1, natrii sulfas 1, rehmanniae radix cervi 2, moutan 1 | Weight loss, improved lipid metabolism, increased heat metabolism, improved constipation, and suppressed fat accumulation effect |
| Soeumin Most frequently complained of low blood sugar symptoms such as dizziness and fatigue during diet | Soeumin prescription for side-effect-preventing powder agent for each constitution: ginseng radix 1, astragali radix 2, atractylodis macrocephalae rhioma 1, cinnamon 1, ginger 1, poria cocos 1, zizyphi fructus1, hawthorn 1, citrus unshiu markovich 1, magnoliae cortex 1 | Immune activity efficacy, Cell protective effect against oxidative stress, hypoglycemic effect, anti-inflammatory effect, treatment for atopic dermatitis, analgesic, sedative effect, parasympathetic effect in the intestine, etc. |

Experimental Example 2 was performed for patients who visited the Korean clinic of the applicant during the 2017 year and prepared an analysis report, wherein the maximum amount of ephedrine content within the range of the US FDA daily allowable ephedrine content was constant at 2.8 to 3.3%, and the weight ratio of ephedra powder, and the stable weight ratio of the side-effect-preventing powder agent for each constitution with respect to the ephedra powder, was different. According to the analysis report of patients who visited the applicant's clinic in 2017, although the amount of the ephedra powder varied depending on the time and location of the ephedra, when the ephedrine content is constant at 3.0-4.0%, about 360 g was in Taeeumin, about 297 g was in Soeumin, and about 360 g was in Soyangin; and when the weight ratio of the constitutional stable side-effect-preventing powder agent with respect to the ephedra powder was 1:8-10 in Taeeumin, 1:9-11 in Soeumin, and 1:8-10 in Soyangin, and when the reduction ratio and side effects were analyzed for 278 patients who visited the applicant's clinic again after taking the composition for each constitution for 3 months, as shown in Table 3 and Table 4, it was determined that the ephedrine content was 3.0-4.0%, indicating a weight effect within the effective range for each constitution.

Table 3 shows the results of experiments of the appropriate weight of ephedra powder by Sasang medical constitution.

TABLE 3

| | | Ephedra powder Weight (g) | | | | | | |
|---|---|---|---|---|---|---|---|---|
| | | 400 | 380 | 360 | 340 | 320 | 300 | 280 |
| Taeeumin | | Appeal for weight loss side effect within effective range | Appeal for weight loss side effect within effective range | Appeal for weight loss side effect within effective range | Insufficient weight loss within effective range | Insufficient weight loss within effective range | Insufficient weight loss within effective range | Insufficient weight loss within effective range |
| Soeumin | | Appeal for weight loss side effect within effective range | Appeal for weight loss side effect within effective range | Appeal for weight loss side effect within effective range | Appeal for weight loss side effect within effective range | Appeal for weight loss side effect within effective range | Appeal for weight loss side effect within effective range | Insufficient weight loss within effective range |
| Soyangin | | Appeal for weight loss side effect within effective range | Appeal for weight loss side effect within effective range | Weight loss within effective range | Insufficient weight loss within effective range | Insufficient weight loss within effective range | Insufficient weight loss within effective range | Insufficient weight loss within effective range |

According to the results of Table 3, the weight of the ephedra powder, which showed the weight loss effect within the effective range for each constitution, was determined when the ephedrine content is constant at 3.0 to 4.0%; and for the weight of the ephedra powder, which showed weight loss within the effective range, it was determined whether side effects did not appear, while showing weight loss within the effective range when the weight of the side-effect-preventing powder agent for each constitution for constitutional stability varied. Here, even a case in which one of the patients who visited the clinic complained of side effects was indicated as the side effect appearance, and the weight loss within the effective range was the case of weight loss less than 5% when measured after 3 months.

Table 4 shows the weight of the side-effect-preventing powder agent by constitution, whether or not weight loss by constitution, and whether or not side effects occurred.

Example 2 was applied and who visited the Korean clinic of the applicant in 2017 showing the results of Table 3 and Table 4, are as follows.

Table 5 is a table summarizing information about the height, initial weight, initial body fat mass, and initial muscle mass of patients who visited the applicant's clinic in 2017.

TABLE 5

| Item | Average | Standard Deviation | Minimum | Maximum |
|---|---|---|---|---|
| Height (cm) | 161.37 | 6.49 | 142.00 | 186.80 |
| Initial weight (kg) | 72.23 | 15.16 | 50.08 | 161.64 |
| Initial body fat mass (kg) | 28.12 | 8.82 | 12.60 | 67.86 |
| Initial muscle mass (kg) | 24.01 | 4.75 | 17.10 | 54.7 |

TABLE 4

| | Constitutional side-effect-preventing powder agent/weight | | | | | | |
|---|---|---|---|---|---|---|---|
| | 20 g | 30 g | 40 g | 50 g | 60 g | 70 g | 80 g |
| Taeeumin/(Ephedra powder 360 g) | Complaint of weight loss side effect within effective range | Complaint of weight loss side effect within effective range | Weight loss within effective range | Insufficient weight loss within effective range | Complaint of insufficient weight loss side effect within effective range | Insufficient weight loss within effective range | Complaint of insufficient weight loss side effect within effective range |
| Soeumin/(Ephedra powder 300 g) | Complaint of weight loss side effect within effective range | Weight loss within effective range | Complaint of weight loss side effect within effective range | Complaint of insufficient weight loss side effect within effective range | Complaint of insufficient weight loss side effect within effective range | Complaint of weight loss side effect within effective range | Complaint of insufficient weight loss side effect within effective range |
| Soyangin/(Ephedra powder 360 g) | Complaint of weight loss side effect within effective range Complaint of weight loss side effect within effective range | Complaint of weight loss side effect within effective range Complaint of weight loss side effect within effective range | Weight loss within effective range Weight loss within effective range | Insufficient weight loss within effective range Weight loss Insufficient weight loss within effective range | Complaint of insufficient weight loss side effect within effective range Insufficient weight loss within effective range | Insufficient weight loss within effective range Insufficient weight loss within effective range | Complaint of insufficient weight loss side effect within effective range Insufficient weight loss within effective range |

That is, in the case of Taeeumin, the weight loss within the effective range was shown for 360 g of ephedra powder, but it was found that when the ratio of the ephedra power and the side-effect-preventing powder agent for each constitution was larger than 8-10:1, there were cases in which weight loss was not achieved within the effective range, and people complaining of side effects appeared.

In addition, in the case of Soeumin, the weight loss within the effective range was shown for 300 g of ephedra powder, but it was found that when the ratio of the ephedra power and the side-effect-preventing powder agent for each constitution was larger than 9-11:1, there were cases in which weight loss was not achieved within the effective range, and people complaining of side effects appeared.

In addition, in the case of Soeumin, the weight loss within the effective range was shown for 300 g of ephedra powder, but it was found that when the ratio of the ephedra power and the side-effect-preventing powder agent for each constitution was larger than 9-11:1, there were cases in which weight loss was not achieved within the effective range, and people complaining of side effects appeared.

Figure 2:
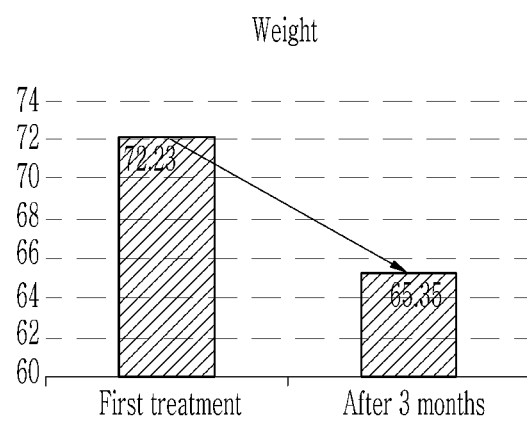
FIG. 2 illustrates a graph analyzing a weight loss ratio after 3 months of taking an herbal medicinal tablet formulation for treating obesity which can be prescribed based on Sasang constitutional medicine according to an embodiment of the present invention.

Meanwhile, the height, initial weight, body fat mass, and initial muscle mass of patients to which Experimental Example 2 was applied and who visited the Korean clinic of Therefore, according to the result of analyzing the weight loss ratio of 278 people after taking the herbal medicinal tablet formulation for treating obesity which can be prescribed based on Sasang constitutional medicine prescribed by considering the weight ratio of the side effects preventing powder agent for each constitution with respect to the ephedra powder agent as in the result of Experimental Example 2 considering each constitution, for 3 months (strictly 10 to 12 weeks), as shown in FIG. 2, the average weight loss was 6.88 kg, and the difference was statistically significant (p-value=0.000).

Success in losing weight in obesity treatment is defined as losing 5 to 10% of weight, and the weight loss ratio of the present composition was 9.37% on average, indicating that it was close to successful weight loss in both medical and clinical aspects.

In addition, as shown in Table 6, 243 patients (87.4%) of the 278 patients lost 5% or more of their body weight, and 115 patients of 278 patients (41.4%) lost 10% or more of their body weight. Therefore, it can be seen that 87.4% (87 out of 100) of the patients who visited Nubebe Korean medicine clinic may lose 5% or more of their weight.

Table 6 is a table showing the percentage distribution of weight loss among patients who visited the applicant's clinic.

TABLE 6

| Classification | Number of patients | Percent |
| --- | --- | --- |
| Weight loss of 5% or more | 243 people | 87.4% |
| Weight loss of 10% or more | 115 people | 41.4% |

Figure 3:
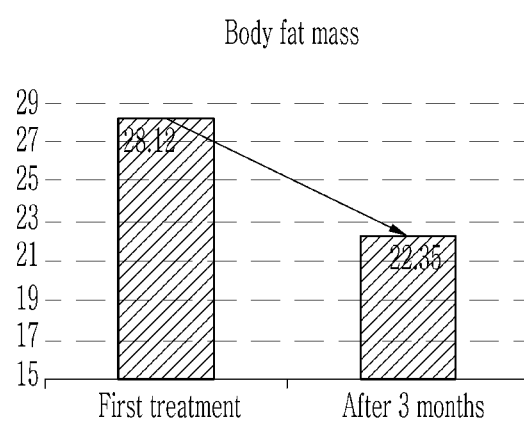
FIG. 3 illustrates a graph analyzing a change in body fat mass after 3 months of taking an herbal medicinal tablet formulation for treating obesity which can be prescribed based on Sasang constitutional medicine according to an embodiment of the present invention.
Figure 3:
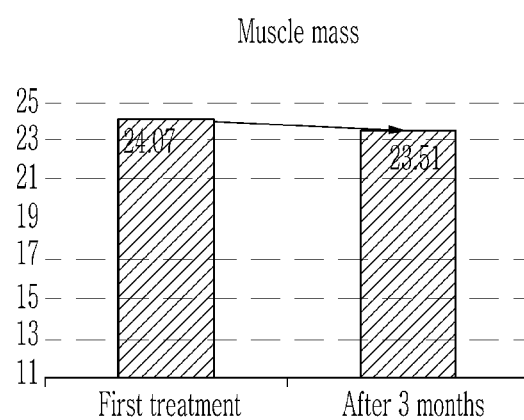

As shown in FIG. 3, as a result of comparing the changes in the initial body fat mass and the body fat mass after 3 months of taking the mediation, an average of 5.77 kg was lost and the difference was statistically significant (p-value=0.000). In the muscle mass, there was an average decrease of 0.56 kg, and there was also a statistically significant difference (p-value=0.000). However, the p-value is a probability value that is affected by a sample size, and tends to approach 0 as the sample size increases. That is, since data with sufficient or large sample sizes may show significant results even for very small differences, it is necessary for an analyst to check the statistical significance and to determine whether there is the substantial significance in the difference in results. In the muscle mass, a change of about 0.56 kg was observed before and after the actual treatment, and clinically, the weight loss effect of the present application may be considered to mainly originate from the body fat loss effect. In addition, as shown in Table 7, patients with normal weight lost an average of 7.99% compared to the first treatment, and patients with high obesity lost an average of 9.89% compared to the first treatment. Although the present composition achieved an effective weight loss effect even at the normal weight, it showed a successful weight loss especially in obese patients (including obesity and high obesity).

Table 7 summarizes the percentage of weight loss with respect to the obesity state of patients who visited the applicant's clinic.

TABLE 7

| Classification | Percentage of weight loss |
| --- | --- |
| Normal | Average weight loss of 7.99% |
| Overweight | Average weight loss of 8.02% |
| Obesity | Average weight loss of 9.36% |
| Extreme obesity | Average weight loss of 9.89% |

In addition, as shown in Table 8, regardless of the degree of obesity, in the analysis by weight band, among the 278 patients, the number of patients in the 50 kg band was 39, the number of patients in the 60 kg band was 117, the number of patients in the 70 kg band was 66, and the number of patients in the 80 kg band was 26, and the number of patients in the 90 kg band and the 100 kg or more band respectively was 15, respectively. Table 8 is a table showing weight loss by weight regardless of obesity.

TABLE 8

| Weight | Average weight loss | Standard deviation of weight loss | Average weight loss ratio | Standard deviation of weight loss ratio |
| --- | --- | --- | --- | --- |
| 50 kg band | 4.74 kg | 1.94 kg | 8.33% | 3.35% |
| 60 kg band | 5.80 kg | 2.28 kg | 8.93% | 3.46% |
| 70 kg band | 7.67 kg | 2.79 kg | 10.25% | 3.55% |
| 80 kg band | 7.75 kg | 4.05 kg | 9.12% | 4.77% |
| 90 kg band | 9.78 kg | 5.26 kg | 10.37% | 5.52% |
| 100 kg band | 12.89 kg | 4.84 kg | 11.06% | 3.88% |
| Total | 6.87 kg | 3.51 kg | 9.37% | 3.81% |

As shown in Table 8, it can be seen that as the weight increased from 50 kg to 100 kg or more, the average weight loss also increased. However, in the average weight loss ratio, it can be seen that the average weight loss ratio of patients of the 70 kg band was 10.25%, which was higher than the weight loss ratio of patients of the 80 kg band. The minimum and maximum values of the weight loss ratio of the patients of the 70 kg band were 3.27% and 20.96%, respectively, and the minimum and maximum values of the weight loss ratio of the patients of the 80 kg band were −0.99% and 18.27%, respectively, wherein the weight loss ratio of some patients was 0.60%. The average weight loss ratio increased to 9.89%, excluding the patients who gained weight and whose weight loss ratio was 0%, among patients of the 80 kg band. Therefore, among the patients of the 80 kg band, there was a patient who gained weight, and it can be seen that this had an effect on the average weight loss ratio. Based on clinical data, the weight loss effect of the present composition was close to successful weight loss in a medical and clinical sense, and considering the time taken, rapid weight loss was achieved in a short period of 10 weeks compared to other medicines (western medicine and herbal medicine).

It can be seen that even in the process of complex preparation, the ephedra was extracted alone; the stability of the medicine was maintained by quantifying the indicator component; the safety of treatment was maintained by adjusting the content of the indicator component in consideration of weight and obesity; and it maintained an excellent treatment rate and reduced the duration of the dose, consequently improving the treatment rate.

On the other hand, among the compositions of the herbal medicinal tablet formulation for treating obesity which can be prescribed based on Sasang constitutional medicine according to the embodiment of the present invention, in general, in the case of Taeeumin, obesity became a sensitive problem, and thus, a lipase inhibitory efficacy test of the herbal medicinal tablet formulation for treating obesity which can be prescribed based on Sasang constitutional medicine for Taeeumin, was performed.

Experimental Example 4

The measurement of lipase activity of the herbal medicinal tablet formulation for treating obesity which can be prescribed based on Sasang constitutional medicine for Taeeumin, was measured using 4-dinitrophenyl butyrate as a substrate.

A porcine pancreatic lipase from Sigma company, USA (0.5 mg/mL), was purchased, and was dissolved in a 0.1 mol potassium phosphate buffer solution, and then, in order to measure the lipase inhibitory efficacy of the herbal medicinal tablet formulation for treating obesity which can be prescribed based on Sasang constitutional medicine for Taeeumin, experiments were performed at five concentrations of 0.04%, 0.08%, 0.12%, 0.16%, and 0.2%, and measured 10 times per concentration.

0.4 mL of 4-dinitrophenyl butyrate solution was added to a mixed solution of the prepared 0.1 mL pancreatic lipase solution and 0.1 mL Gambijeong M solution, and 0.1 mL of 1M Tris-HCL solution was added thereto, and then it was reacted for 5 minutes at 37° C. in an incubator.

Then, the activity of the lipase was determined by measuring the absorbance of 4-dinitrophenol isolated by the lipase with a spectrophotometer at 360 nm.

The experimental results were represented as relative values of the lipase to the control at 100%, and the experimental result was found to be significant when the P value was 0.05% or less through the statistical program SPSS, as shown in Table 9 and Table 10.

Table 9 is raw data of the lipase activity.

TABLE 9

| | 1 | 2 | 3 | 4 | 5 | 6 | 7 | 8 | 9 | 10 |
|---|---|---|---|---|---|---|---|---|---|---|
| CON | 22.43334 | 22.18817 | 22.67852 | 22.92369 | 22.92369 | 22.8011 | 22.8011 | 22.67852 | 22.67852 | 22.67852 |
| Pan | 103.2179 | 101.1339 | 100.0306 | 99.41771 | 99.04995 | 99.90806 | 99.66289 | 99.5403 | 100.3984 | 99.66289 |
| S_0.04 | 96.72081 | 101.1339 | 103.9534 | 104.5663 | 104.3212 | 102.3598 | 102.1146 | 102.7276 | 102.605 | 103.4631 |
| S_0.08 | 82.25559 | 89.51079 | 93.04321 | 93.04321 | 90.46889 | 91.44959 | 93.53356 | 93.53356 | 91.93993 | 91.93993 |
| S_0.12 | 83.60405 | 80.53936 | 85.68802 | 83.84922 | 82.25559 | 83.35887 | 85.32026 | 84.58474 | 84.9525 | 90.95924 |
| S_0.16 | 88.50751 | 81.52007 | 80.04903 | 78.82317 | 82.13301 | 82.86853 | 81.88783 | 82.37818 | 83.72663 | 82.50077 |
| S_0.20 | 85.07508 | 77.47472 | 79.31352 | 77.47472 | 76.61661 | 78.08765 | 79.19093 | 81.64266 | 85.32026 | 84.58474 |

Table 10 is a table showing the lipase activity with respect to "Gambijeong" for Taeeumin.

TABLE 10

| Density | Lipase activity |
|---|---|
| 0.00% | 100.20 ± 1.14 |
| 0.04% | 102.50 ± 2.17 |
| 0.08% | 91.05 ± 3.19 |
| 0.12% | 84.51 ± 2.73 |
| 0.16% | 82.44 ± 2.55 |
| 0.20% | 80.48 ± 3.41 |

Figure 4:
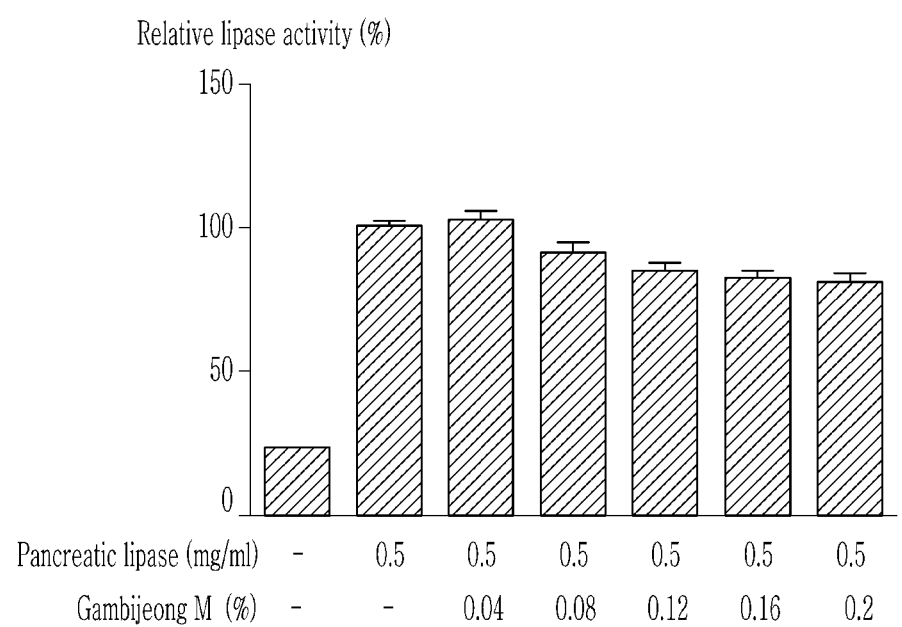
FIG. 4 illustrates a graph analyzing a lipase inhibitory ability test of an herbal medicinal tablet formulation for treating obesity which can be prescribed based on Sasang constitutional medicine according to an embodiment of the present invention.

As shown in Table 10 and FIG. 4, the herbal medicinal tablet formulation for treating obesity which can be prescribed based on Sasang constitutional medicine for Taeeumin showed significant lipase inhibitory ability from a 0.08% concentration, and it was also found that inhibiting lipase efficacy in the body could be utilized to lower the body's utilization of fat when taken with a high fat diet.

On the other hand, from the experimental results for patients who visited the Korean clinic of the applicant, the patient's obesity (or BMI) and the usage of the composition based on the constitution could be standardized as shown in Table 11 by using the daily content of ephedrine.

Table 11 shows the constitutional usage of the herbal medicinal tablet formulation for treating obesity which can be prescribed based on Sasang constitutional medicine according to the embodiment of the present invention, wherein Gambijeong 1 to Gambijeong 4 represent the division by the constitution of the herbal medicinal tablet formulation for treating obesity.

TABLE 11

| Classification | Ephedrine content (1 day) | Usage |
|---|---|---|
| Gambijeong 1 | 60-90 mg | Normal weight, overweight, initial obesity |
| Gambijeong 2 | 80-120 mg | Overweight, obesity |
| Gambijeong 3 | 90-120 mg | Moderate and severe obesity |
| Gambijeong 4 | 130-140 mg | Immunity, moderate, and high obesity |

Figure 5:
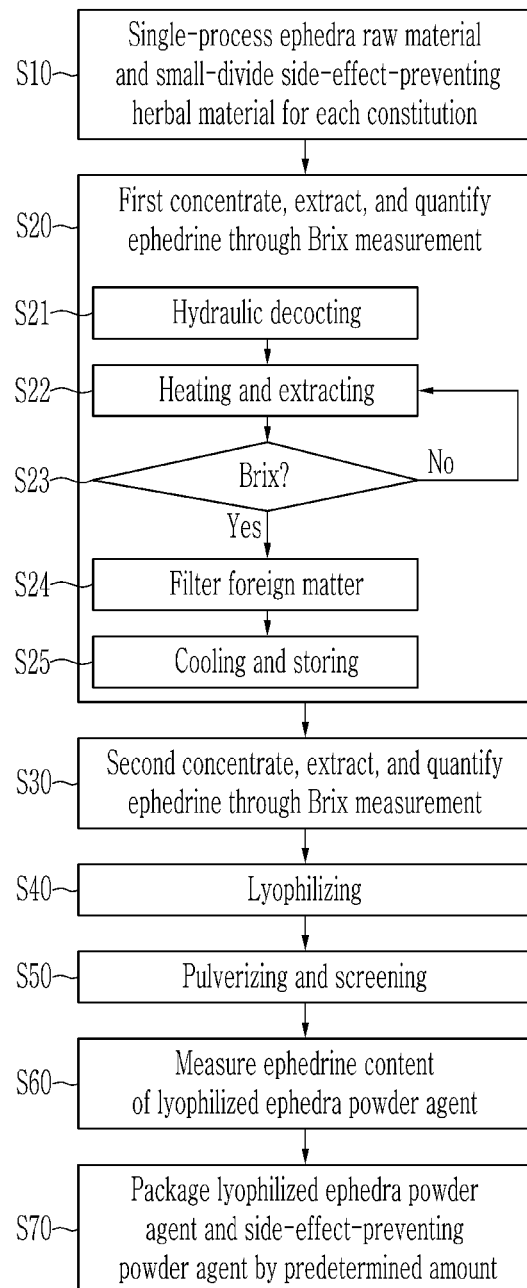
FIG. 5 illustrates a flowchart of a manufacturing method of an ephedra powder agent for an herbal medicinal tablet formulation for treating obesity which can be prescribed based on Sasang constitutional medicine according to an embodiment of the present invention, and a side-effect-preventing powder agent, by constitution.
Figure 6:
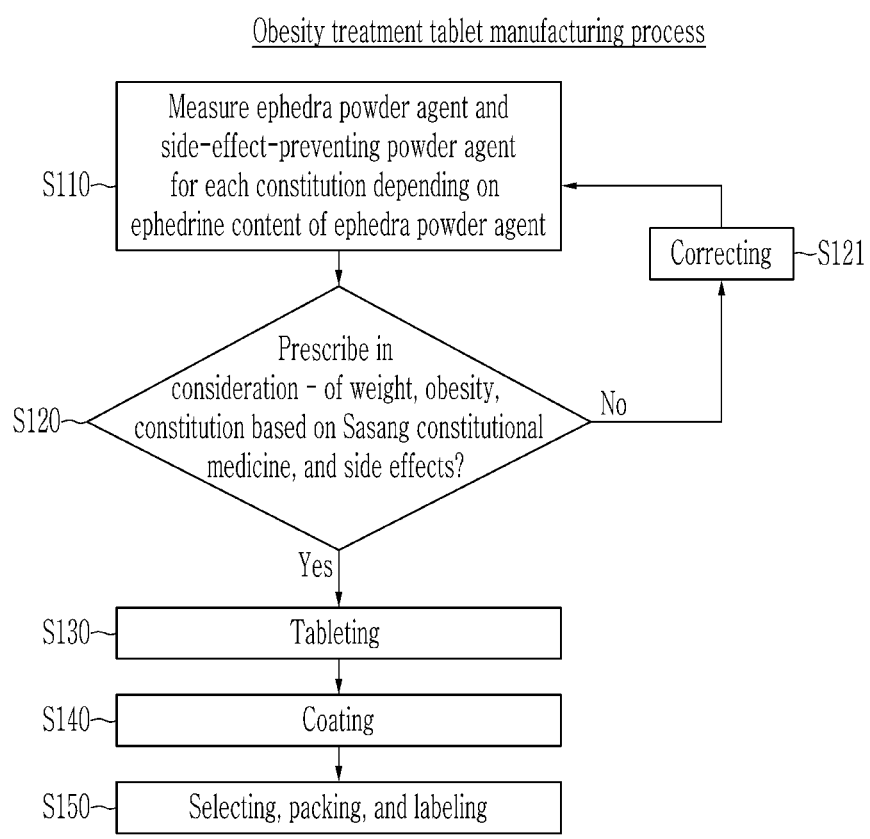
FIG. 6 illustrates a flowchart of a manufacturing method of an herbal medicinal tablet formulation for treating obesity which can be prescribed based on Sasang constitutional medicine according to an embodiment of the present invention.

A manufacturing method of an herbal medicinal tablet formulation for treating obesity which can be prescribed based on Sasang constitutional medicine will now be described in detail with reference to FIG. 5 to FIG. 11. FIG. 5 illustrates a flowchart of a manufacturing method of an ephedra powder agent for an herbal medicinal tablet formulation for treating obesity which can be prescribed based on Sasang constitutional medicine according to an embodiment of the present invention, and a side-effect-preventing powder agent by constitution, FIG. 6 illustrates a flowchart of a manufacturing method of an herbal medicinal tablet formulation for treating obesity which can be prescribed based on Sasang constitutional medicine according to an embodiment of the present invention, FIG. 7 to FIG. 9 respectively illustrate a graph of measuring an ephedrine content every 2 hours for 10 lots in a decocting process for 4 different ephedra with different producing districts and collecting periods so as to manufacture an ephedra powder agent for an herbal medicinal tablet formulation for treating obesity which can be prescribed based on Sasang constitutional medicine according to an embodiment of the present invention, and FIG. 10 and FIG. 11 respectively illustrate graphs for explaining a pattern relationship between a Brix content and an ephedrine content in manufacturing an ephedra powder agent for an herbal medicinal tablet formulation for treating obesity which can be prescribed based on Sasang constitutional medicine according to an embodiment of the present invention, by using the results shown in FIG. 7 to FIG. 9.

Figure 7:
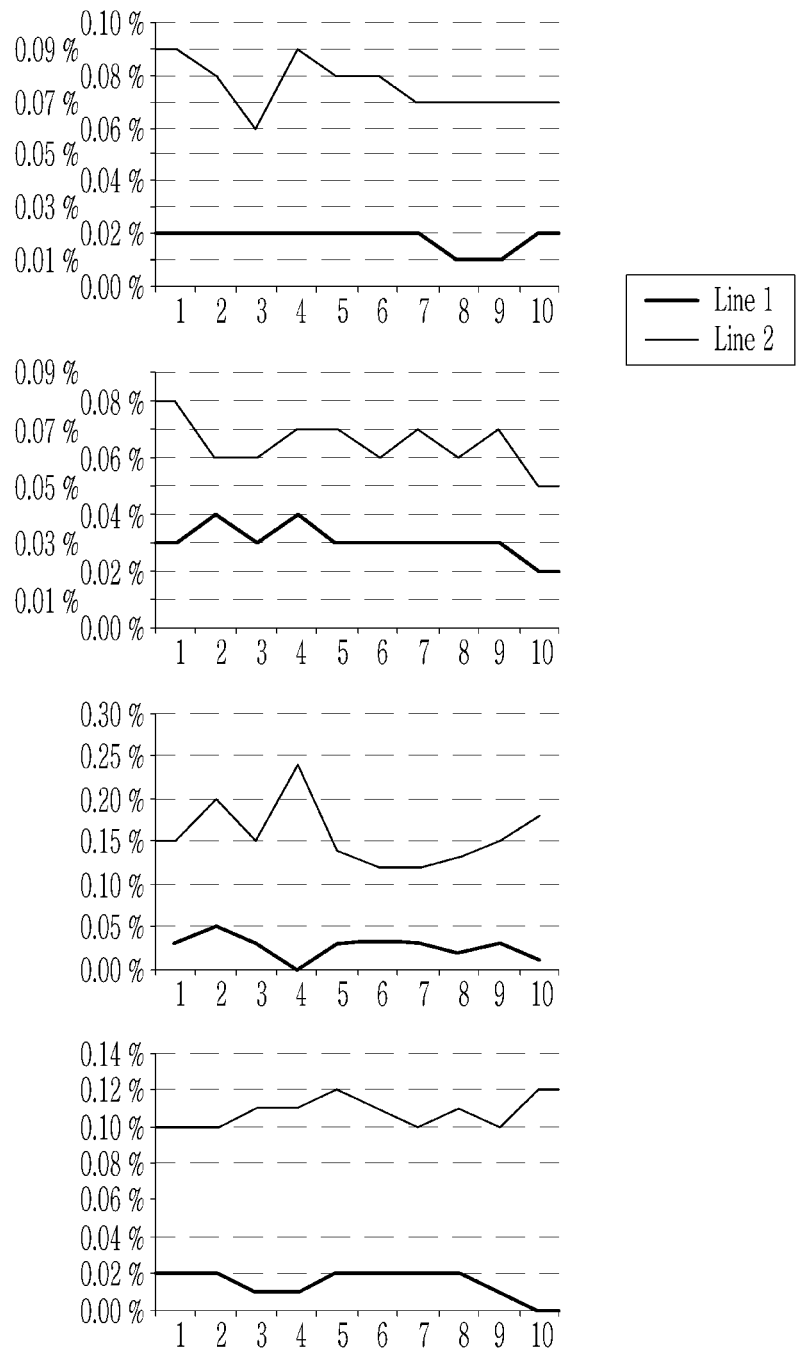
FIG. 7 to FIG. 9 respectively illustrate graphs for measuring an ephedrine content every 2 hours for 10 lots in a decocting process for 4 different ephedra with different producing districts and collecting periods so as to manufacture an ephedra powder agent for an herbal medicinal tablet formulation for treating obesity which can be prescribed based on Sasang constitutional medicine according to an embodiment of the present invention.
Figure 8:
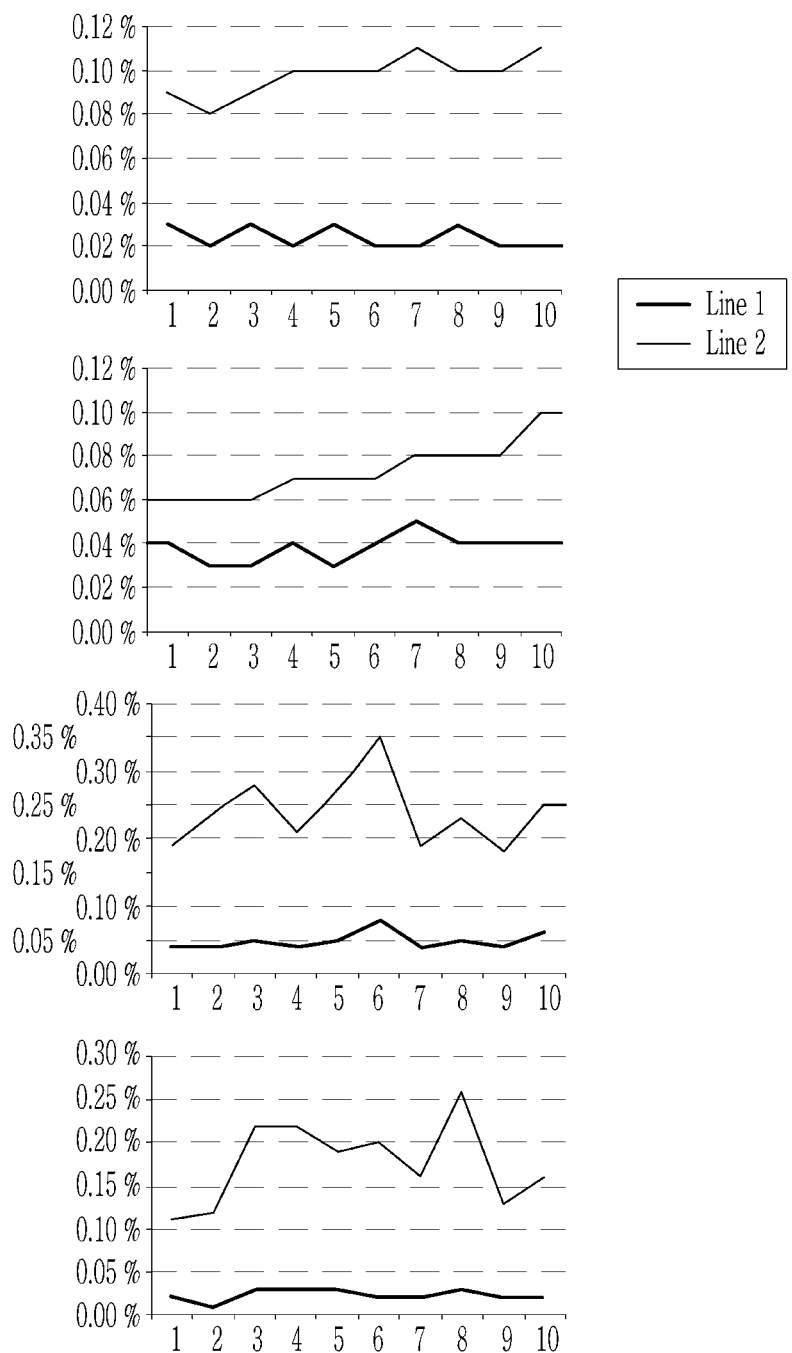
Figure 9:
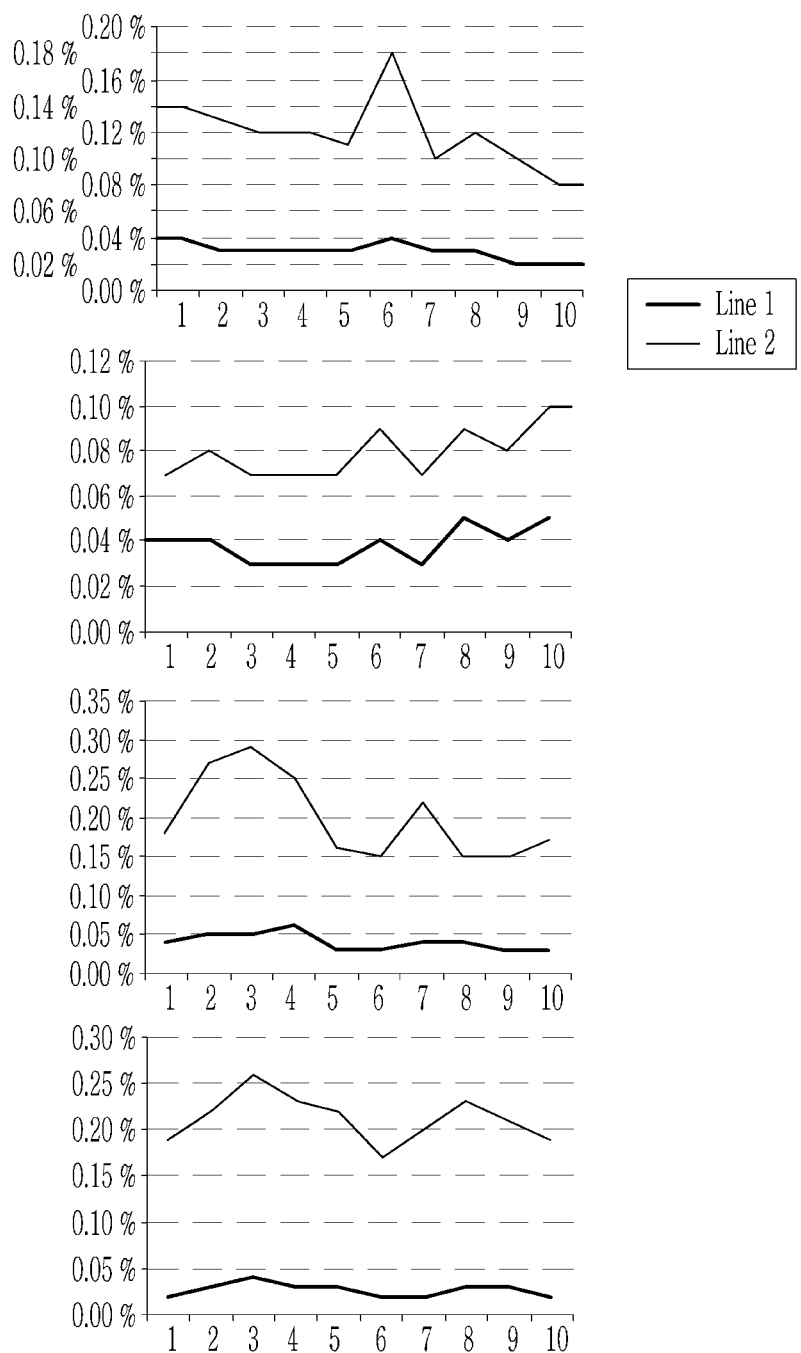

In FIG. 7 to FIG. 9, line 1 is pseudoephedrine content %, and line 2 is ephedrine content %.

Generally, the herbal medicines are provided in various ways, such as decoctions, pills, powders, granule preparations, concentrated liquid preparations, and distillation agents, however, they are not suitable as a treatment for obesity, such as by having a peculiar smell, bitter taste, stickiness, or feeling of satiety due to excessive amounts, which are peculiar to herbal medicine preparations, and therefore, the manufacturing method of the herbal medicinal tablet formulation for treating obesity which can be prescribed based on Sasang constitutional medicine according to the embodiment of the present invention provides a tablet formulation for treating obesity that may be prescribed according to Sasang constitutional medicine so as to solve the above problems and achieve the obesity treatment effect without side effects according to the prescription for each constitution based on Sasang constitutional medicine.

As shown in FIG. 7 and Table 12, first, the ephedrine content of ephedra was 0.185 for spring collection in China and 0.360 for collection in Pakistan, depending on the producing district and collecting period, wherein a difference between their content % was almost doubled by 0.09% and 0.18%, and thus, it can be seen that they did not reach 2.8 to 3.3% that were an amount of being able to treat obesity within 3 months.

Table 12 show data for four ephedra of different producing districts and collecting periods.

TABLE 12

| Extraction time | Experimental material | Place of origin | Weight of extraction liquid | | | | | | Brix Measure |
|---|---|---|---|---|---|---|---|---|---|
| | | | Vessel | Raw material | Total weight | Extraction liquid weight | Extraction rate | Average | |
| 6 hr | S1-1 | Chinese spring | 174.73 | 30.00 | 313.02 | 108.29 | 36.1% | 136.40 | 6.4% |
| | S1-2 | | 176.00 | 30.00 | 324.15 | 118.15 | 39.4% | | 6.1% |
| | S1-3 | | 181.65 | 30.00 | 343.16 | 131.51 | 43.8% | | 5.3% |
| | S1-4 | | 189.65 | 30.00 | 354.27 | 134.62 | 44.9% | | 5.2% |
| | S1-5 | | 172.79 | 30.00 | 346.64 | 143.85 | 48.0% | | 4.8% |
| | S1-6 | | 146.20 | 30.00 | 265.85 | 89.65 | 29.9% | | 8.3% |
| | S1-7 | | 174.74 | 30.00 | 369.29 | 164.55 | 54.9% | | 4.4% |
| | S1-8 | | 176.02 | 30.00 | 333.31 | 127.29 | 42.4% | | 5.6% |
| | S1-9 | | 181.65 | 30.00 | 376.73 | 165.08 | 55.0% | | 4.6% |
| | S1-10 | | 189.65 | 30.00 | 400.67 | 181.02 | 60.3% | | 4.0% |
| | S2-1 | Chinese autumn | 172.80 | 30.00 | 378.30 | 175.50 | 58.5% | 164.77 | 3.8% |
| | S2-2 | | 146.19 | 30.00 | 336.60 | 160.41 | 53.5% | | 4.1% |
| | S2-3 | | 174.74 | 30.00 | 355.28 | 150.54 | 50.2% | | 4.5% |
| | S2-4 | | 176.01 | 30.00 | 397.11 | 191.10 | 63.7% | | 3.5% |
| | S2-5 | | 181.67 | 30.00 | 388.45 | 176.78 | 58.9% | | 3.8% |
| | S2-6 | | 189.66 | 30.00 | 373.35 | 153.69 | 51.2% | | 4.3% |
| | S2-7 | | 172.87 | 30.00 | 415.24 | 212.37 | 70.8% | | 3.2% |
| | S2-8 | | 146.18 | 30.00 | 317.20 | 141.02 | 47.0% | | 4.6% |
| | S2-9 | | 174.74 | 30.00 | 372.42 | 167.68 | 55.9% | | 3.9% |
| | S2-10 | | 176.00 | 30.00 | 324.61 | 118.61 | 39.5% | | 5.2% |
| | S3-1 | Pakistan | 181.64 | 30.00 | 357.51 | 145.87 | 48.6% | 160.64 | 6.0% |
| | S3-2 | | 189.64 | 30.00 | 317.80 | 98.16 | 32.7% | | 8.1% |
| | S3-3 | | 172.80 | 30.00 | 299.95 | 97.15 | 32.4% | | 8.2% |
| | S3-4 | | 146.19 | 30.00 | 299.02 | 122.83 | 40.9% | | 7.0% |
| | S3-5 | | 174.73 | 30.00 | 411.89 | 207.16 | 69.1% | | 4.3% |
| | S3-6 | | 176.01 | 30.00 | 415.79 | 209.78 | 69.9% | | 4.2% |
| | S3-7 | | 181.66 | 30.00 | 354.54 | 142.88 | 47.6% | | 6.1% |
| | S3-8 | | 189.64 | 30.00 | 428.12 | 208.48 | 69.5% | | 4.4% |
| | S3-9 | | 172.79 | 30.00 | 398.96 | 196.17 | 65.4% | | 4.5% |
| | S3-10 | | 146.18 | 30.00 | 354.08 | 177.90 | 59.3% | | 5.0% |
| | S4-1 | Kyrgyzstan | 174.75 | 30.00 | 347.54 | 142.79 | 47.6% | 123.90 | 6.2% |
| | S4-2 | | 182.70 | 30.00 | 332.59 | 119.89 | 40.0% | | 7.2% |
| | S4-3 | | 168.83 | 30.00 | 290.56 | 91.73 | 30.6% | | 9.2% |
| | S4-4 | | 186.91 | 30.00 | 329.61 | 112.70 | 37.6% | | 7.7% |
| | S4-5 | | 179.74 | 30.00 | 327.90 | 118.16 | 39.4% | | 7.2% |
| | S4-6 | | 146.19 | 30.00 | 326.11 | 149.92 | 50.0% | | 5.8% |
| | S4-7 | | 174.73 | 30.00 | 338.70 | 133.97 | 44.7% | | 6.3% |
| | S4-8 | | 182.69 | 30.00 | 316.97 | 104.28 | 34.8% | | 7.5% |
| | S4-9 | | 168.82 | 30.00 | 320.16 | 121.34 | 40.4% | | 7.0% |
| | S4-10 | | 186.90 | 30.00 | 361.13 | 144.23 | 48.1% | | 6.1% |

| Extraction time | Average | Total alkaloid | | | | Extraction amount Total correction | Extraction amount Total correction Average |
|---|---|---|---|---|---|---|---|
| | | Pseudo Ephedrine | Ephedrine | Dose | Dose Average | | |
| 6 hr | 5.5% | 0.04% | 0.14% | 0.18% | 0.15% | 0.28% | 0.27% |
| | | 0.03% | 0.13% | 0.16% | | 0.26% | |
| | | 0.03% | 0.12% | 0.15% | | 0.27% | |
| | | 0.03% | 0.12% | 0.15% | | 0.27% | |
| | | 0.03% | 0.11% | 0.14% | | 0.27% | |
| | | 0.04% | 0.18% | 0.22% | | 0.31% | |
| | | 0.03% | 0.10% | 0.13% | | 0.29% | |
| | | 0.03% | 0.12% | 0.15% | | 0.26% | |
| | | 0.02% | 0.10% | 0.12% | | 0.27% | |
| | | 0.02% | 0.08% | 0.10% | | 0.25% | |
| | 4.1% | 0.04% | 0.07% | 0.11% | 0.12% | 0.27% | 0.26% |
| | | 0.04% | 0.08% | 0.12% | | 0.26% | |
| | | 0.03% | 0.07% | 0.10% | | 0.20% | |
| | | 0.03% | 0.07% | 0.10% | | 0.28% | |
| | | 0.03% | 0.07% | 0.10% | | 0.24% | |

TABLE 12-continued

|      | | | | | | |
|------|-------|-------|-------|-------|-------|-------|
|      | 0.04% | 0.09% | 0.13% |       | 0.27% |       |
|      | 0.03% | 0.07% | 0.10% |       | 0.34% |       |
|      | 0.05% | 0.09% | 0.14% |       | 0.26% |       |
|      | 0.04% | 0.08% | 0.12% |       | 0.27% |       |
|      | 0.05% | 0.10% | 0.15% |       | 0.25% |       |
| 5.8% | 0.04% | 0.18% | 0.22% | 0.24% | 0.43% | 0.53% |
|      | 0.05% | 0.27% | 0.32% |       | 0.48% |       |
|      | 0.05% | 0.29% | 0.34% |       | 0.50% |       |
|      | 0.06% | 0.25% | 0.31% |       | 0.52% |       |
|      | 0.03% | 0.16% | 0.19% |       | 0.61% |       |
|      | 0.03% | 0.15% | 0.18% |       | 0.60% |       |
|      | 0.04% | 0.22% | 0.26% |       | 0.50% |       |
|      | 0.04% | 0.15% | 0.19% |       | 0.62% |       |
|      | 0.03% | 0.15% | 0.18% |       | 0.52% |       |
|      | 0.03% | 0.17% | 0.20% |       | 0.49% |       |
| 7.0% | 0.02% | 0.19% | 0.22% | 0.24% | 0.42% | 0.41% |
|      | 0.03% | 0.22% | 0.32% |       | 0.53% |       |
|      | 0.04% | 0.26% | 0.34% |       | 0.49% |       |
|      | 0.03% | 0.23% | 0.31% |       | 0.50% |       |
|      | 0.03% | 0.22% | 0.19% |       | 0.31% |       |
|      | 0.02% | 0.17% | 0.18% |       | 0.36% |       |
|      | 0.02% | 0.20% | 0.26% |       | 0.47% |       |
|      | 0.03% | 0.23% | 0.19% |       | 0.29% |       |
|      | 0.03% | 0.21% | 0.18% |       | 0.30% |       |
|      | 0.02% | 0.19% | 0.20% |       | 0.39% |       |

Therefore, it is necessary to concentrate and quantify the active ingredient in order to extract ephedrine, which is an active ingredient of the herbal medicinal tablet formulation for treating obesity which can be prescribed based on Sasang constitutional medicine according to the embodiment of the present invention, only from the natural component ephedra.

Here, the quantifying is for maintaining the ephedrine content of ephedra powder at a predetermined value, and a sugar measure, Brix, is used. Brix is precisely called Brix %, and this unit is an amount of solute dissolved in an aqueous solution as a unit of %, and it is a "soluble solid", which means that a high Brix is high in a soluble solid, including salt, protein, acid, and the like as well as a sugar content, and it can be used as a measure of the ratio of ephedrine content by measuring very widely used Brix.

To this end, the method for manufacturing the ephedra powder agent and side-effect-preventing powder agent for each constitution for the herbal medicinal tablet formulation for treating obesity which can be prescribed based on Sasang constitutional medicine according to the embodiment of the present invention includes: small-dividing each of the ephedra for ephedra powder and the herbal ingredients prescribed for the side-effect-preventing powder agent for each constitution shown in Table 2, based on the weight per pack (S10); and primarily concentrating and quantifying ephedrine, which is an active ingredient, through the Brix measurement while undergoing a hydraulic decocting process (S20).

The hydraulic decocting process, which is a process of facilitating the decocting by applying hydraulic pressure, generally includes: after washing with water, immersing in water at a temperature of 10 to 20° C., about 10 times for each weight, for 15 to 20 hours, to increase extraction of the active ingredient (S21); and then boiling each material at a temperature of 95 to 100° C. for 4 to 5 hours to extract an extract liquid having a high yield (S21); measuring Brix every heating time (S23); checking whether the extract liquid has 7 Brix or more (S24); when the Brix of the extract liquid is not more than 7 Brix, the heating time is increased, while when the Brix of the extract liquid is more than 7 Brix, filtering foreign materials using a nanofilter of 100 mesh (S25); and maintaining cooling at 40 to 50° C. to prevent microorganisms and storing it while stirring it to prevent precipitation of solids (S26).

Figure 10:
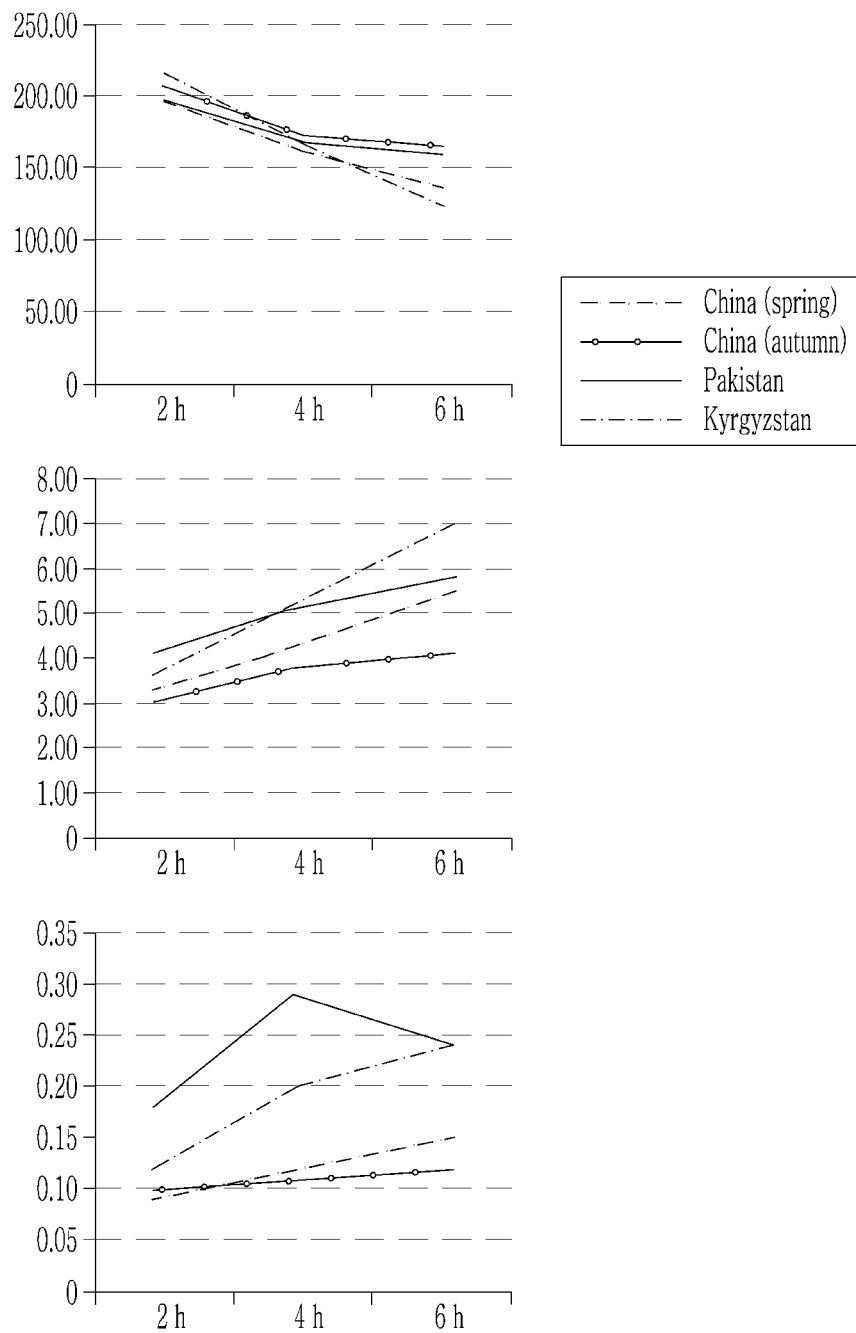
FIG. 10 and FIG. 11 respectively illustrate graph for explaining a pattern relationship between a Brix content and an ephedrine content in manufacturing an ephedra powder agent for an herbal medicinal tablet formulation for treating obesity which can be prescribed based on Sasang constitutional medicine according to an embodiment of the present invention, by using the results shown in FIG. 7 to FIG. 9.
Figure 11:
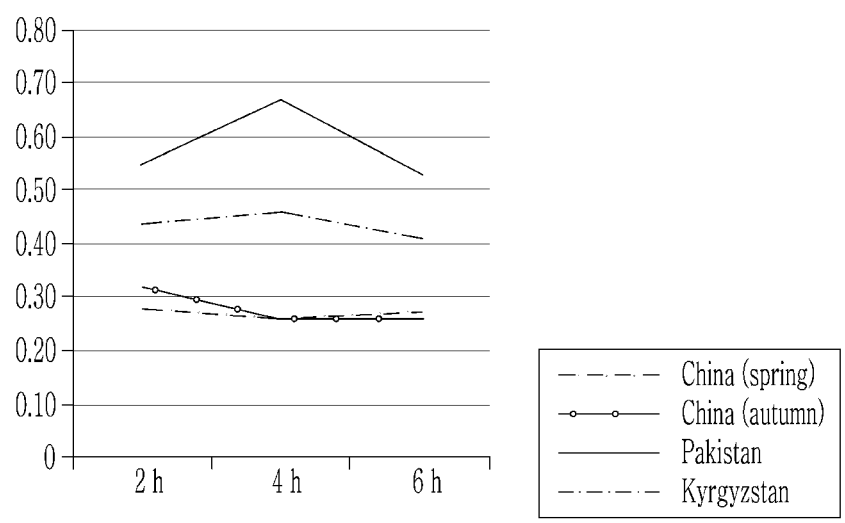
Figure 11:
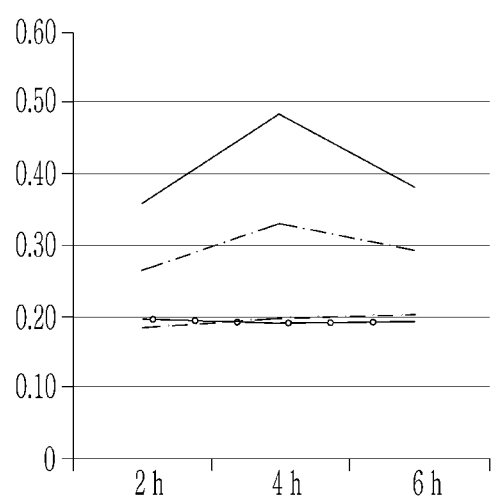

In the method for manufacturing the ephedra powder agent and side-effect-preventing powder agent for each constitution for the herbal medicinal tablet formulation for treating obesity which can be prescribed based on Sasang constitutional medicine according to the embodiment of the present invention, the reason for primarily quantifying the ephedrine to 7 Brix or more using the hydraulic decocting process was that the Brix substantially increased with the heating time of the hydraulic decocting process as shown in FIGS. 10 and 11, but the ephedrine content of ephedra remained constant at approximately 7 Brix even if the producing districts and collecting periods of the ephedra were different, or it had a pattern of decreasing by pressure or temperature, thus there was no need to use unnecessary energy in a situation in which the yield of the active ingredient was kept constant.

Experimental Example 5

The Brix measurement in the hydraulic decocting process and the content measurement of ephedrine in each Brix value were performed as follows.

For four ephedra (by country of origin-made in China, Pakistan, Kyrgyzstan/by collecting period-Chinese spring and autumn harvest), namely S1 (Chinese, spring), S2 (Chinese, autumn), S3 (Pakistan), and S4 (Kyrgyzstan), the same specimen was divided into 10 batches and tested; the extraction conditions were 10 times the weight of the test material, and after heating, the extract was made every 2 hours from the point of 100° C.; the weight of each extract was calculated by weight (extract weight=total weight-container weight-raw material weight); the Brix value for each lot was measured using a Brix densitometer called a Refractometer, ATAGO PAL-1; and the total alkaloid and ephedrine contents were measured using HPLC and Shimadzu 20-A series.

[Quantity Test]

Measured as a total alkaloid [ephedrine ($C_{10}H_{15}NO$: 165.23 g/mol) and pseudoephedrine ($C_{10}H_{15}NO$: 165.23 g/mol)], standard solution: ephedrine hydrochloride (dried at 105° C. for 3 hours in advance), approximately 50 mg of the standard product is precisely weighed, and diluted methanol (1→2) is added thereto to make exactly 20 mL. 2 mL of this solution is accurately taken, and diluted methanol (1→2) is added thereto to make exactly 100 mL.

Test solution: About 5 mL of the extract is precisely weighed, put it in a stoppered centrifuge tube, and 20 mL of diluted methanol (1→2) is added thereto and shaken for 30 minutes, and then is centrifuged to take the supernatant.

Next, in order to maintain each material at a predetermined concentration, it is boiled at a temperature of 95 to 100° C. and extracted until the concentration reached 7 to 10 Brix for secondary quantification. 20 mL of methanol (1→2) diluted in the residue is again used, and the above operation is repeated twice. All the extracts are combined, and the diluted methanol (1→2) is added thereto to make exactly 100 mL.

Detector: UV absorbing photometer (measurement wavelength 210 nm)

Column: a stainless steel pipe having an inner diameter of 4-6 mm and a length of 15-20 cm is filled with 5-10 μm octadecylsilyl silica gel for liquid chromatography.

Constant temperature around 45° C.

Mobile phase: sodium lauryl sulfate solution (1→128) *acetonitrile*phosphate mixture (640:360:1)

The results are shown in Table 13 and Table 14.

TABLE 13

| Brix (% Brix) | 2 h | 4 h | 6 h |
| --- | --- | --- | --- |
| China (spring) | 3.30 | 4.30 | 5.50 |
| China (autumn) | 3.00 | 3.80 | 4.10 |
| Pakistan | 4.10 | 5.10 | 5.80 |
| Kyrgyzstan | 3.60 | 5.30 | 7.00 |

TABLE 14

| Total alkaloid (%) | 2 h | 4 h | 6 h |
| --- | --- | --- | --- |
| China (spring) | 0.28 | 0.26 | 0.27 |
| China (autumn) | 0.32 | 0.26 | 0.26 |
| Pakistan | 0.55 | 0.67 | 0.53 |
| Kyrgyzstan | 0.44 | 0.46 | 0.41 |

As can be seen from Table 13 and Table 14, according to the hydraulic decocting process, it is about 0.41% on average at 7 Brix, and the content of ephedrine is insufficient to make 3 to 4% of the ephedrine powder agent, and in the case of continuous heating, destruction of active ingredients such as ephedrine occurs, and thus, secondary ephedrine concentration extraction and quantification is performed using a vacuum low-temperature concentration process (S30).

In order to again concentrate the extract extracted in the hydraulic decocting process at a high concentration while lowering the heating temperature and increasing the concentration rate under reduced pressure and in a vacuum, under reduced pressure conditions, the extract is vacuum-reduced and concentrated for 5 to 6 hours under the reduced pressure condition of 08 to 09 bar and the concentration temperature of 50° C. to 55° C.

Meanwhile, even in this case, the concentration is also maintained constant using the Brix, and while confirming whether the concentration of each material becomes approximately 30 to 35 Brix, it is secondarily quantified to prepare a concentrate.

Here, in order to increase and maintain the ephedrine content %, it is determined using a Brix densitometer whether the concentration of the ephedra concentrate is 30 to 35 Brix, and the reason is that, as shown in Table 15, the total alkaloid correction average content % also increases with an increase in the Brix according to a vacuum decompression container, but thereafter, in lyophilization, crystals are generated in the case of 10 to 20 Brix, or the ephedrine content is rather lowered under the influence of temperature and pressure in the case of 40 Brix or more.

In addition, it was also possible to concentrate it up to 30 Brix through the hydraulic decocting process, but in this case, as described above, the content of ephedrine was reduced by heat, and the concentration time was increased by 2 to 3 times or more.

Table 15 is a table summarizing problems that occur when the Brix increases through a hydraulic decocting process.

TABLE 15

|  | 10 Brix | 20 Brix | 30 Brix | 40 Brix | 50 Brix |
| --- | --- | --- | --- | --- | --- |
| Total alkaloid correction average content % | 1.1% | 1.9% | 2.8% | 3.5% | 5% |
| Problem | Crystal generation during lyophilization | Crystal generation during lyophilization | Close to effective ephedrine content | Ephedrine content reduction (temperature, pressure effect) | Ephedrine content reduction (temperature, pressure effect) |

The ephedrine is secondarily concentrated and quantified by the vacuum low-temperature concentration process, and the averaged concentrate is lyophilized (freeze-dried) by mixing different concentrates for each lot and each batch (S40). The lyophilization is a drying method that removes moisture using the property of sublimating only the moisture in the sample when the sample is frozen and then reduced in pressure, and according to the lyophilization, compared to simple hot air drying, wind drying, or high temperature drying, the dried material contains a myriad of gaps, so it is easy to absorb moisture, so it is easy to rehydrate quickly and completely.

Therefore, the herbal medicinal tablet formulation for treating obesity which can be prescribed based on Sasang constitutional medicine according to the embodiment of the present invention has the effect of being disintegrated within 30 minutes when taken with water.

Meanwhile, the ephedra concentrate concentrated at 30 to 35 Brix may also drop the ephedrine content %, which is the active ingredient of the ephedra concentrate, according to the freezing temperature and freezing time, and thus, after performing an experiment to find a suitable freezing temperature and time, the ephedrine content % was measured to confirm whether it was reduced.

The concentrate of the secondary quantified concentrated at 2.8% ephedrine content was divided into 3000 ml trays of a lyophilizer, and the temperature and freezing time were varied to measure the ephedrine content % and shown in Table 16.

Table 16 is a table showing a change in ephedrine content % according to a freezing temperature and a time.

TABLE 16

| Temperature (° C.) | −0 to −10° C. | −10 to −20° C. | −20 to −30° C. | −30 to −40° C. | −40 to −50° C. | −50 to −60° C. |
|---|---|---|---|---|---|---|
| Time (h) | 18 hours | 14 hours | 10 hours | 8 hours | 5 hours | 3 hours |
| Total alkaloid correction average content | 2.8% | 2.78% | 2.77% | 2.8% | 2.5% | 2.41% |

As a result of the test, it is determined that the freezing time at a temperature of −40 to −50° C. is suitable in terms of a time of 3 to 5 hours, but it is suitable to freeze it at −30 to −40° C. for 8 hours, which may be maintained within the error range even if it takes a long time to maintain the total alkaloid corrected average content %, that is, ephedrine content %.

Subsequently, drying proceeds, and at this time, in order to preserve the ephedrine content % well, the experiment results are shown in Table 17 while varying the drying temperature, pressure, and time.

Table 17 shows a change in ephedrine content % according to a drying condition.

TABLE 17

| Item | 01 | 02 | 03 | 04 | 05 | 06 | 07 |
|---|---|---|---|---|---|---|---|
| Temperature (° C.) | −30 | −20 | −10 | 0 | 10 | 20 | 30 |
| Pressure (mb) | 50 | 50 | 50 | 5 | 5 | 0 | 0 |
| Time (h) | 12 hours | 18 hours | 24 hours | 28 hours | 32 hours | 48 hours | 60 hours |
| Total alkaloid correction average content | 2.31% | 2.50% | 2.52% | 2.55% | 2.56% | 2.6% | 2.81% |

As can be seen from Table 17, when the lyophilization was performed under the freezing condition at a temperature of −30 to −40° C. and a freezing time of 8 hours and the drying condition at a temperature of 30 to 40° C. and a freezing time of at least 60 hours, the active ingredient of the concentrated liquid was well preserved, and a high concentration and yield of the ephedra powder agent was obtained.

The lyophilized phase dried in the lyophilization process (S40) was pulverized to make a powder of a 40 to 45 mesh size, and then screened with a sieve of 40 to 45 mesh to screen the pulverized powder medicine to a certain size (S50).

The ephedrine content of the ephedra powder agent, which was a powder medicine of a predetermined size, prepared as described above, was measured (S60), and then predetermined amounts of the ephedra powder agent and the herbal medicine powder agent for each side-effect-preventing powder agent were hermetically packaged in bags (S70).

A manufacturing method of the herbal medicinal tablet formulation for treating obesity which can be prescribed based on Sasang constitutional medicine according to the embodiment of the present invention will now be described in detail with reference to FIG. 6.

In the manufacturing method of the herbal medicinal tablet formulation for treating obesity which can be prescribed based on Sasang constitutional medicine according to the embodiment of the present invention, the ephedra powder agent and the side-effect-preventing powder agent for each constitution are measured and mixed depending on the ephedrine content of the ephedra powder agent (S110).

In this case, the prescription is checked by referring to a list of the patient's weight, obesity, constitution based on Sasang constitutional medicine, side effects, and the like (S120), and when it is necessary to correct the prescription, the amount of the side-effect-preventing powder agent for each constitution with respect to the amount of the ephedra powder agent or the weight of the ephedra powder agent is corrected within the range of 1:8-10 to 1:9-11 (S121).

When the checking and correcting of the prescription are not required with reference to the list of the patient's weight, obesity, constitution based on Sasang constitutional medicine, side effects, and the like, in order to prepare tablet formulations such as croscarmellose sodium, microcrystalline cellulose, and magnesium stearate, which act as disintegrants or hardness agents, the subsidiary material is mixed and put into the tableting apparatus, and then as shown in FIG. 1, it is tableted to have a size having a thickness of 590±010 mm, a diameter of 176±020 mm, and a weight of 646 mg±50% (S130).

After the tableting process (S130), in order to prevent the active ingredient from being destroyed when exposed to air, it is coated by installing the coating liquid in the fixed frame of the injector, opening the liquid adjustment nozzle of each injector, increasing the pressure of the liquid pump to 1 to 2 bar, letting the initial liquid flow for 3 minutes, and then adjusting the pressure and the amount of air in the liquid pump (S140).

The coating condition is a 60-250 ml/min liquid volume at a speed of 2-7 rpm at a pressure of 5-6 kg/cm$^2$ with a 12 Fmm nozzle size.

It is coated with the coating solution and then cooled and dried at 25-30° C. for 20 minutes at a low speed; defective products are taken off, and the pills are packed in containers accommodating 90 tablets so as to be able to be taken three times a day for three months; and a label on which patient, constitution, ephedrine content %, and prescription information for each constitution is recorded is attached to the container.

Experimental Example 6

To confirm that the herbal medicinal tablet formulation for treating obesity manufactured by the manufacturing method of the herbal medicinal tablet formulation for treating obesity which can be prescribed based on Sasang Medicine according to an embodiment of the present invention was effective in reducing obesity, 93 subjects were dosed for 10 days or 5 days, respectively, and the appetite suppressing effect, convenience when taking it, absorption rate, and preference were checked.

Although the content of the herbal medicine for each constitution was different, when confirming the results for the present invention, there was no variation for each constitution.

Experiment Method (1) After 3 months of taking it, 4 kinds of appetite suppression effects such as "none, normal, existence, and very good" were confirmed.

(2) In order to check the convenience when taking it, the convenience degree as 4 kinds of "none, normal, existence, and very good" was confirmed from those who have taken the existing herbal decoction or capsule.

(3) In order to check the absorption rate, the convenience degree as 4 kinds of "none, normal, existence, and very good" was confirmed from those who have taken the existing herbal decoction or capsule.

(4) In order to check the overall preference, 4 preferences of "none, normal, existence, and very good" was confirmed from those who have taken the existing herbal decoction or capsule.

Since the composition of the herbal medicinal tablet formulation (Gambijeong) for treating obesity which can be prescribed based on Sasang constitutional medicine according to the embodiment of the present invention mainly reduces body fat, it is first checked through experiments whether it has the clinical effectiveness of weight loss for Sasang constitution, whether the Gambitang composition as a decoction medicine is stable for Taeeumin, and whether there is a clinical effect of weight loss without side effects.

Table 18 shows an experimental result of a clinical effect of Gambijeong on Taeeumin.

TABLE 18

| | Appetite suppression effect | Convenience | Absorption rate | Preference |
|---|---|---|---|---|
| Very good | 39 | 64 | 51 | 50 |
| Existence | 30 | 39 | 38 | 27 |
| Normal | 19 | 0 | 3 | 5 |
| None | 5 | 0 | 1 | 1 |
| Total | 93 | 93 | 93 | 93 |

As can be seen in Table 18, the appetite suppression effect was found to be effective in 69 (74%) out of 93 patients; the convenience was found to be effective in 93 (100%) out of 93 patients; the absorption rate, which was improved compared to that of the existing decoction or capsule, was found to be effective in 89 (95%) out of 93 patients; and the overall preference was found to be effective in 77 (82%) out of 93 patients. It was confirmed that the herbal medicinal tablet formulation and manufacturing method for treating obesity which can be prescribed based on Sasang Medicine according to the embodiment of the present invention were more convenient, preferred, and improved in absorption rate compared to other methods of taking the traditional herbal medicine, and it was confirmed that the herbal medicine according to Example 6 had the appetite suppression effect.

INDUSTRIAL APPLICABILITY

The herbal medicinal tablet formulation and manufacturing method for treating obesity which can be prescribed based on Sasang Medicine according to the embodiment of the present invention, since it is advantageous in that the herbal medicine varies in the content of the drug according to the constitution and the degree of the disease, even for the same disease, and thus the prescription varies, may provide the advantage of the herbal medicine, and may provide convenience and effective effects to a person taking it by increasing and quantifying the yield of the active ingredient.

In addition, the herbal medicinal tablet formulation and manufacturing method for treating obesity which can be prescribed based on Sasang Medicine according to the embodiment of the present invention may provide an herbal medicine with low stability to be more convenient to take and to be quickly absorbed.

While this invention has been described in connection with what is presently considered to be practical exemplary embodiments, it is to be understood that the invention is not limited to the disclosed embodiments.

The invention claimed is:

1. A manufacturing method of an herbal medicinal tablet formulation for treating obesity which can be prescribed based on Sasang constitutional medicine, comprising:
    manufacturing a concentrated ephedra powder agent so that an ephedrine content is 3.0-4.0% from an initial ephedra of which initial ephedrine content ranges 0.5-2.5% depending on a producing district and collecting period;
    manufacturing a side effect-preventing powder agent for each Sasang constitution to prevent and suppress side effects of the ephedrine that are anticipated or known for each Sasang constitution;
    mixing the concentrated ephedra powder agent and the side effect-preventing powder agent with a variance of a weight ratio therebetween in consideration of weight, obesity, constitution of Sasang constitutional medicine, and side effects;
    tableting the mixture of the concentrated ephedra powder agent and side effect-preventing powder agent;
    coating the tablets;
    after the coating, sorting out defective ones from the coated tablets; and
    packaging the coated tablets with a label including information prepared according to weight, obesity, constitution of Sasang constitutional medicine, and side effects,
    wherein
    the side effect-preventing powder agent for Taeeumin comprises alisma, platycodon, puerariae, acorus gramineus, castanea mollissima, coicis semen, semen raphani, semen armeniacae amarum, cinnamon-vine and semen nelumbinis, the side effect-preventing powder agent for Soyangin comprises talcum, plaster, peppermint, gardeniae fructus, schizonepeta, rhubarb, natrii sulfas, rehmanniae radix cervi and moutan, and the side effect-preventing powder agent for Soeumin comprises ginseng radix, astragali radix, atractylodis macrocephalae rhioma, cinnamon, ginger, poria cocos, zizyphi fructus, hawthorn, Citrus unshiu Markovich and magnoliae cortex, wherein in the mixing the concentrated ephedra powder agent and the side effect-preventing power agent, when the ephedrine content is constant at 3-4%, a weight of the concentrated ephedra powder agent is about 360 g for Taeeumin, about 297 g for Soeumin, and about 360 g for Soyangin, and a weight ratio of the side effect-preventing powder agent for each constitution with respect to a weight of the concentrated ephedra powder agent is about 1:8-10 for Taeeumin, about 1:9-11 for Soeumin, and about 1:8-10 for Soyangin.

2. The manufacturing method of the herbal medicinal tablet formulation for treating obesity which can be prescribed based on Sasang constitutional medicine of claim 1, wherein the manufacturing of the concentrated ephedra powder agent includes primarily quantifying the ephedrine content in a decoction to be 7 to 8 Brix through Brix measurement every 2 hours in a hydraulic decocting process; and secondarily quantifying the ephedrine content in the decoction to be 30 to 35 Brix through Brix measurement every 2 hours in a vacuum concentration process performed at a temperature from 50° C. to 55° C.

3. The manufacturing method of the herbal medicinal tablet formulation for treating obesity which can be prescribed based on Sasang constitutional medicine of claim 2, further comprising filtering the decoction through a sieve with a 45 mesh scale to separate out solids larder than the 45 mesh scale after the secondarily quantifying.

4. The manufacturing method of the herbal medicinal tablet formulation for treating obesity which can be prescribed based on Sasang constitutional medicine of claim 2, wherein the manufacturing of the concentrated ephedra powder agent further includes lyophilizing the decoction to produce the concentrated ephedra powder agent of 30 to 35 Brix that is secondarily quantified, and in the lyophilizing, a freezing condition is 8 hours at a temperature of −30 to −40° C., and a drying condition is at least 60 hours at a temperature of 30 to 40° C.

5. The manufacturing method of the herbal medicinal tablet formulation for treating obesity which can be prescribed based on Sasang constitutional medicine of claim 4, further comprising measuring and labeling an ephedrine content of the concentrated ephedra powder agent, and airtightly packing the concentrated ephedra powder agent and the side effect-preventing powder agent after the lyophilizing the decoction to produce the concentrated ephedra powder agent and before the mixing the concentrated ephedra powder agent and the side effect-preventing powder agent.

* * * * *